United States Patent [19]
Hall et al.

[11] Patent Number: 4,560,499
[45] Date of Patent: Dec. 24, 1985

[54] ISOSOLANONE AND SOLANONE INTERMEDIATES AND ORGANOLEPTIC USES

[75] Inventors: John B. Hall, Rumson; James M. Sanders, Eatontown; James N. Siano, Keyport, all of N.J.

[73] Assignee: International Flavors & Fragrances Inc., New York, N.Y.

[21] Appl. No.: 609,349

[22] Filed: Jun. 22, 1984

Related U.S. Application Data

[62] Division of Ser. No. 542,477, Oct. 17, 1983, Pat. No. 4,476,147, which is a division of Ser. No. 380,542, May 20, 1982, Pat. No. 4,433,695.

[51] Int. Cl.[4] ................................................ C11B 9/00
[52] U.S. Cl. ............................. 252/522 R; 252/8.6; 252/174.11; 252/522 A; 424/69; 424/70
[58] Field of Search ............... 252/8.6, 174.11, 522 A, 252/522 R; 424/69, 70

[56] References Cited

U.S. PATENT DOCUMENTS

| 2,838,576 | 6/1958 | Normant | 252/522 R X |
| 3,258,497 | 6/1966 | Lemberg | 252/522 R X |
| 3,700,717 | 10/1972 | Kappeler et al. | 252/522 R X |
| 3,997,577 | 12/1976 | von Fraunberg | 252/522 R X |
| 4,347,388 | 8/1982 | Gramlich et al. | 252/522 R X |

Primary Examiner—Thomas A. Waltz
Attorney, Agent, or Firm—Arthur L. Liberman

[57] ABSTRACT

Described is a novel genus of compounds defined according to the structure:

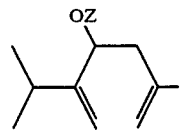

wherein Z represents hydrogen, MgX and the moiety having the structure:

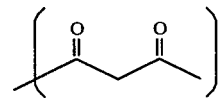

and X represents chloro, bromo or iodo; as well as the novel compounds defined according to the structures:

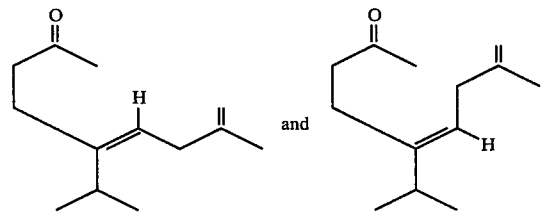

and mixtures of same shown according to the structure

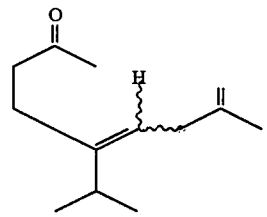

wherein the wavy lines indicate both cis and trans juxtaposition of the hydrogen and methallyl moieties about the carbon-carbon double bond; uses of same as intermediates in a process for producing isosolanone which is a mixture of compounds having the structures:

(Abstract continued on next page.)

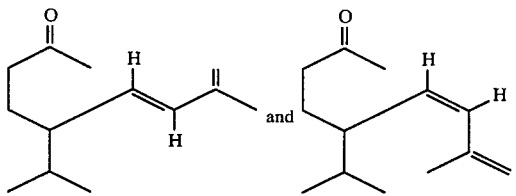
or shown by the structure:
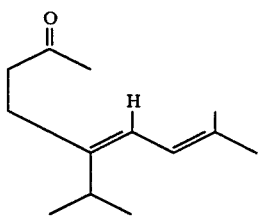 and 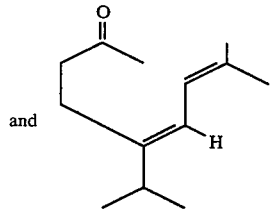
or shown by the single structure:
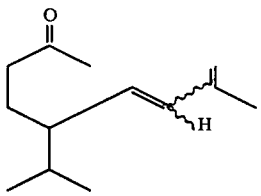
wherein the wavy lines are indicative of a cis or trans juxtaposition of the hydrogen or 2-propenyl moieties about the double bond; and organoleptic uses of the compounds having the structures:
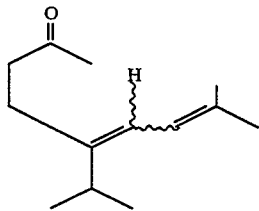
and solanone which is a mixture of compounds having the structures:
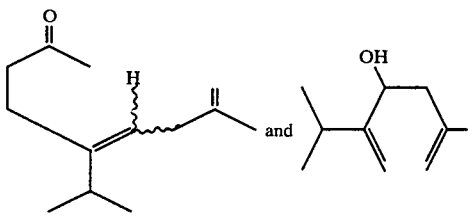
8 Claims, 16 Drawing Figures

GLC PROFILE FOR BULKED FRACTIONS 5-7 OF EXAMPLE II.

GLC PROFILE FOR EXAMPLE I.

NMR SPECTRUM FOR FRACTION 2 OF EXAMPLE I.

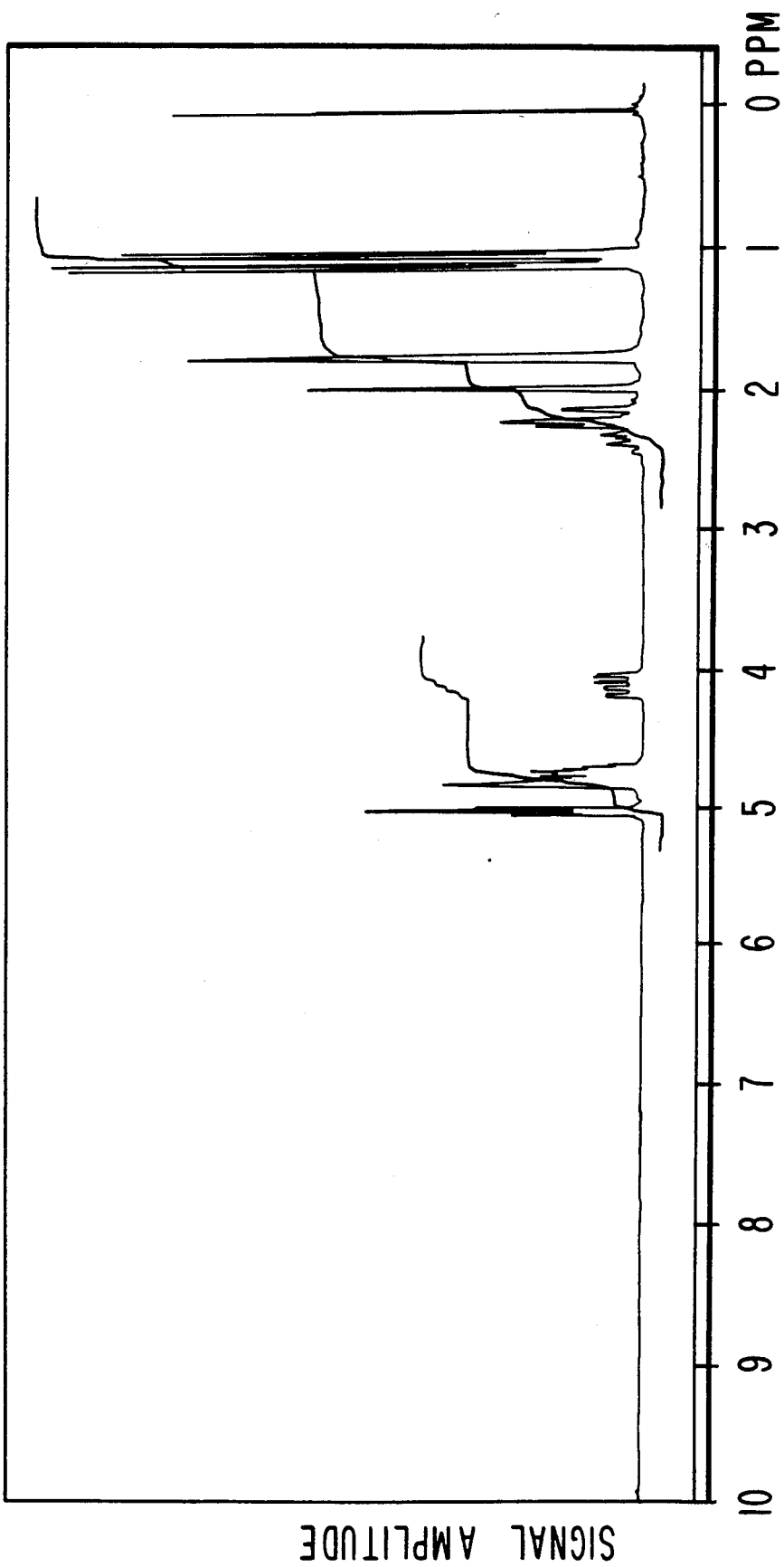

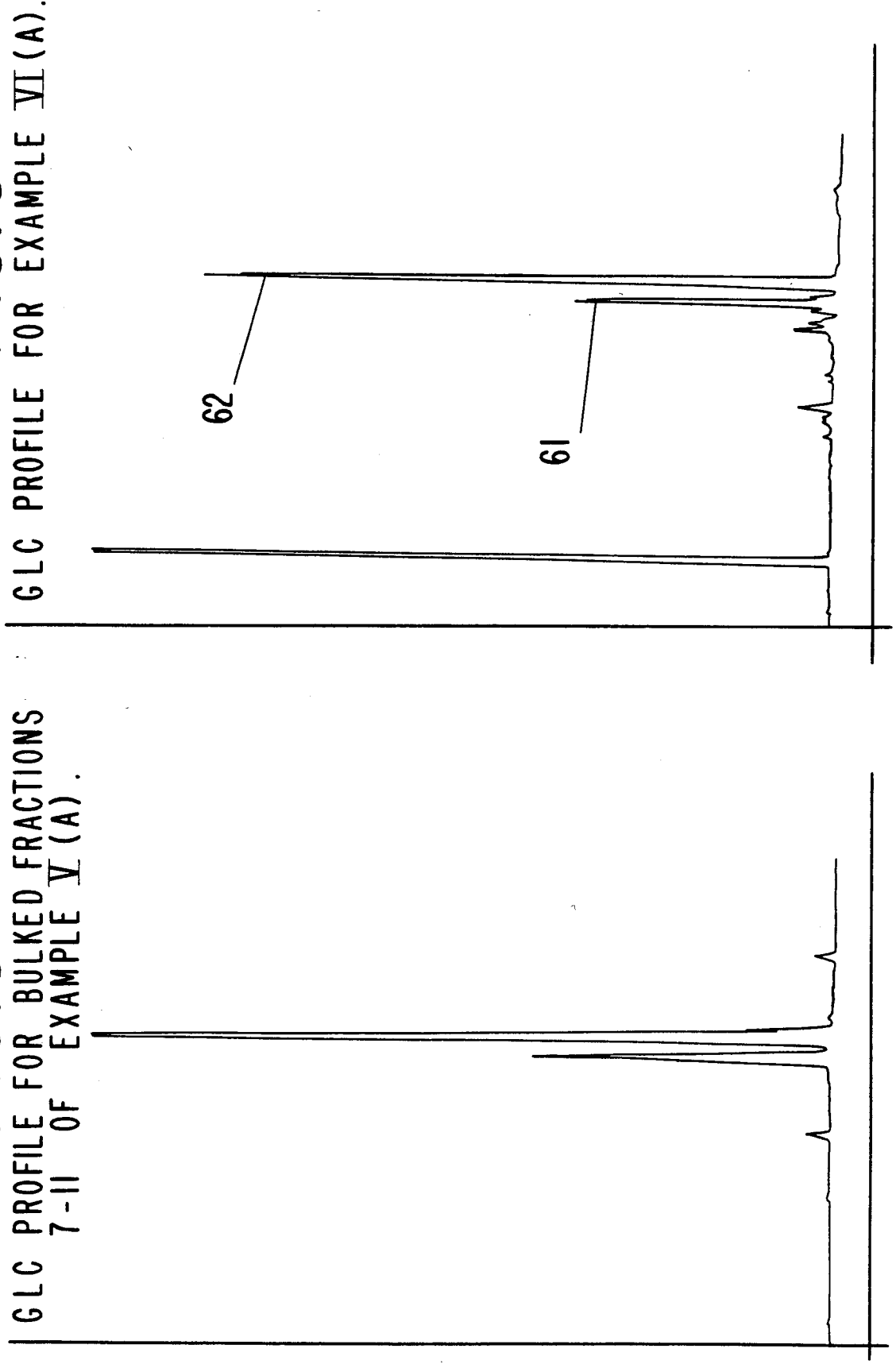

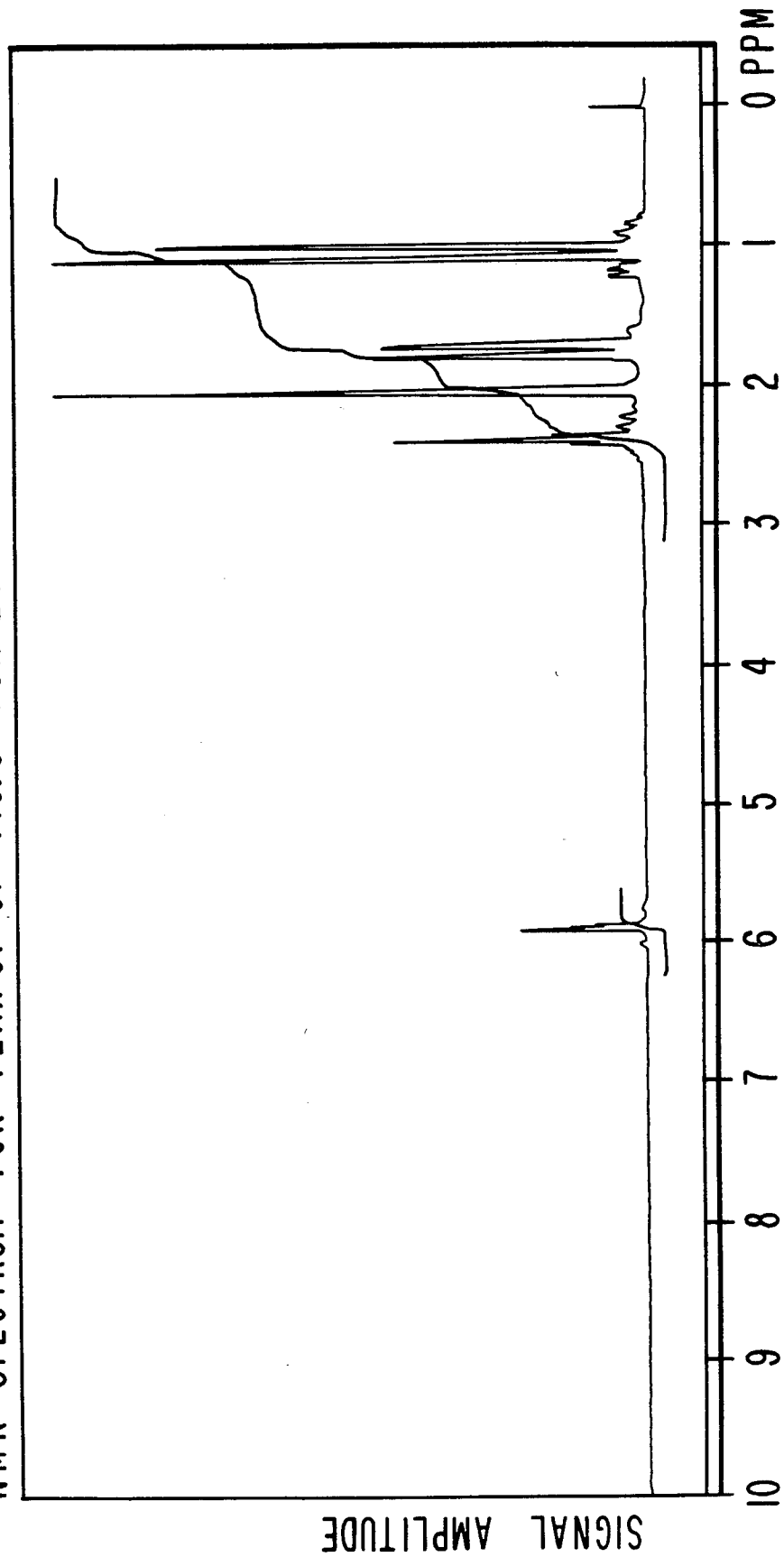

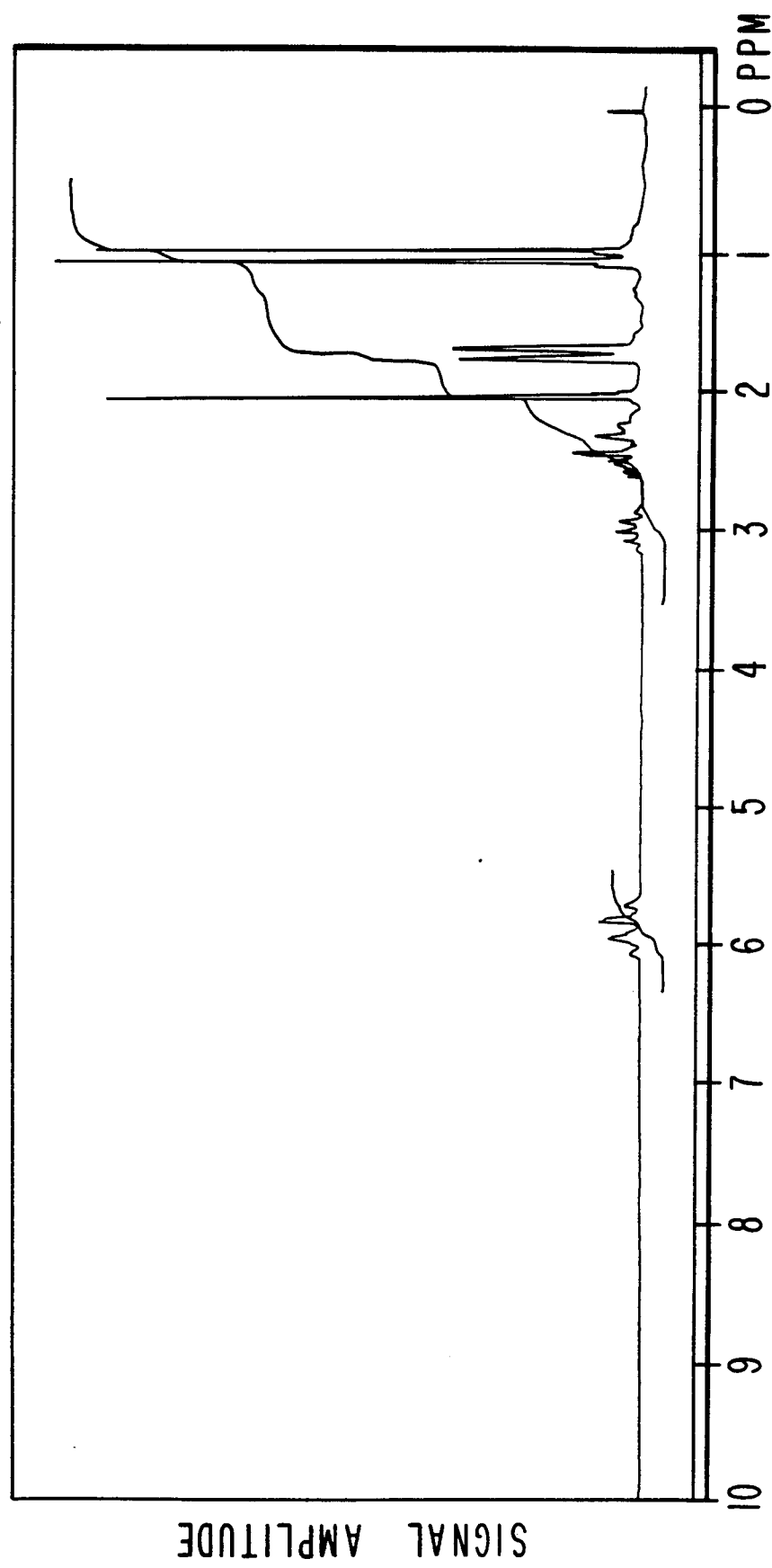

GLC PROFILE FOR EXAMPLE VII(B) BULKED FRACTION 4-11.

91

GLC PROFILE FOR EXAMPLE VII (A).

NMR SPECTRUM FOR PEAK 91 OF FIG. 9 FOR EXAMPLE VII (A).

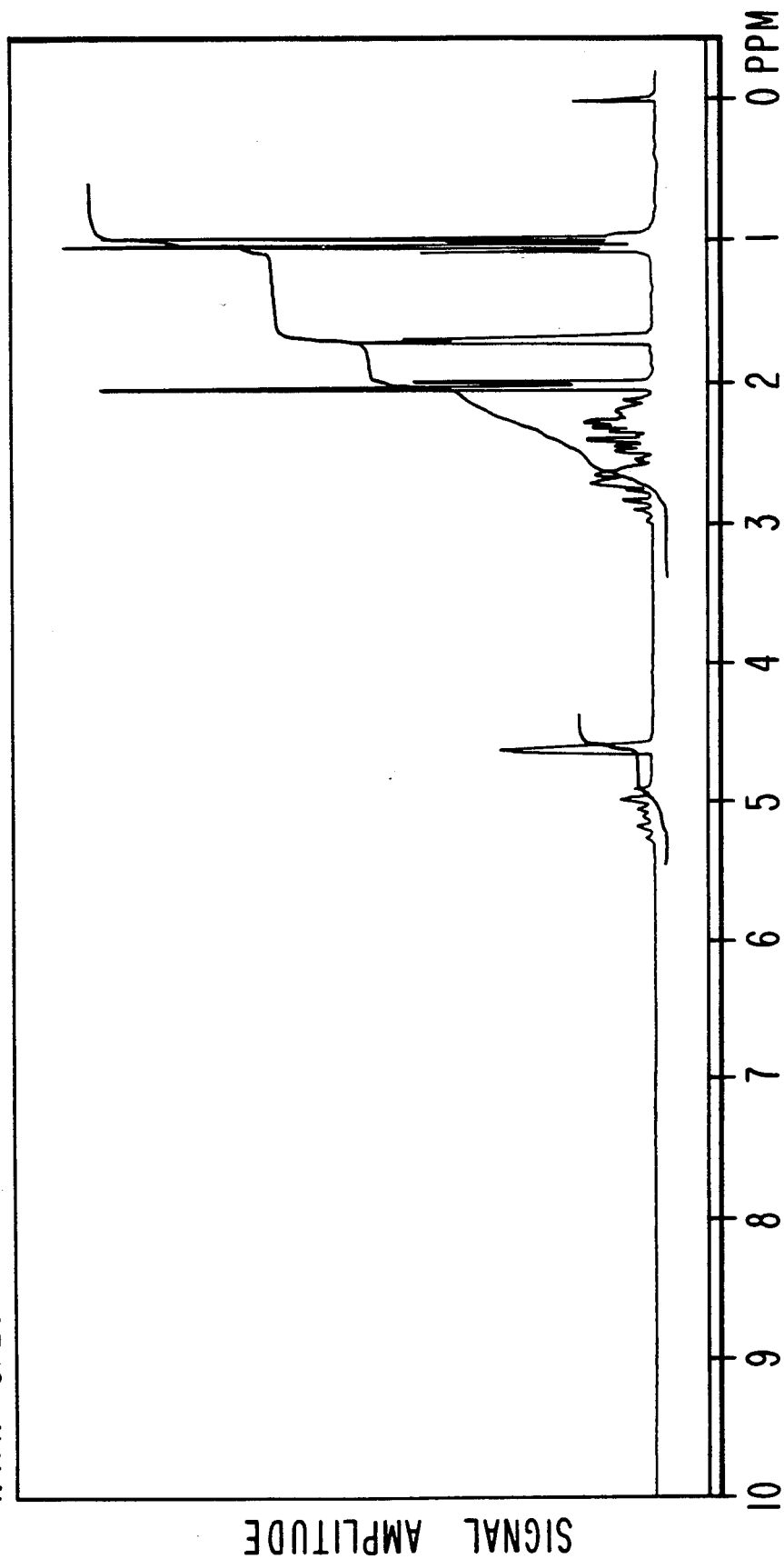
FIG.12 NMR SPECTRUM FOR FRACTION 7 OF EXAMPLE VII (B).

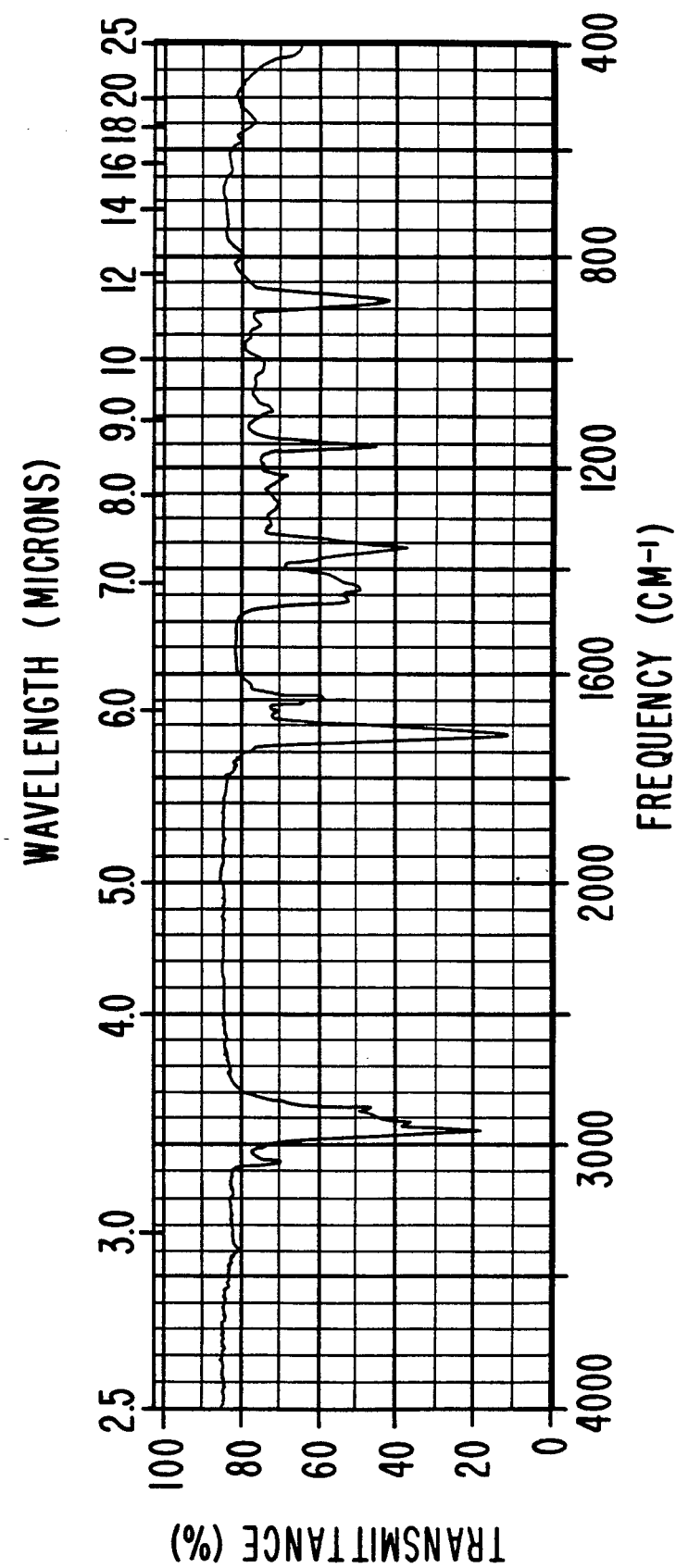

GLC PROFILE BULKED FRACTIONS 9-12.
FOR EXAMPLE IX.

NMR SPECTRUM FOR PEAK 141 OF FIG.14 FOR EXAMPLE IX.

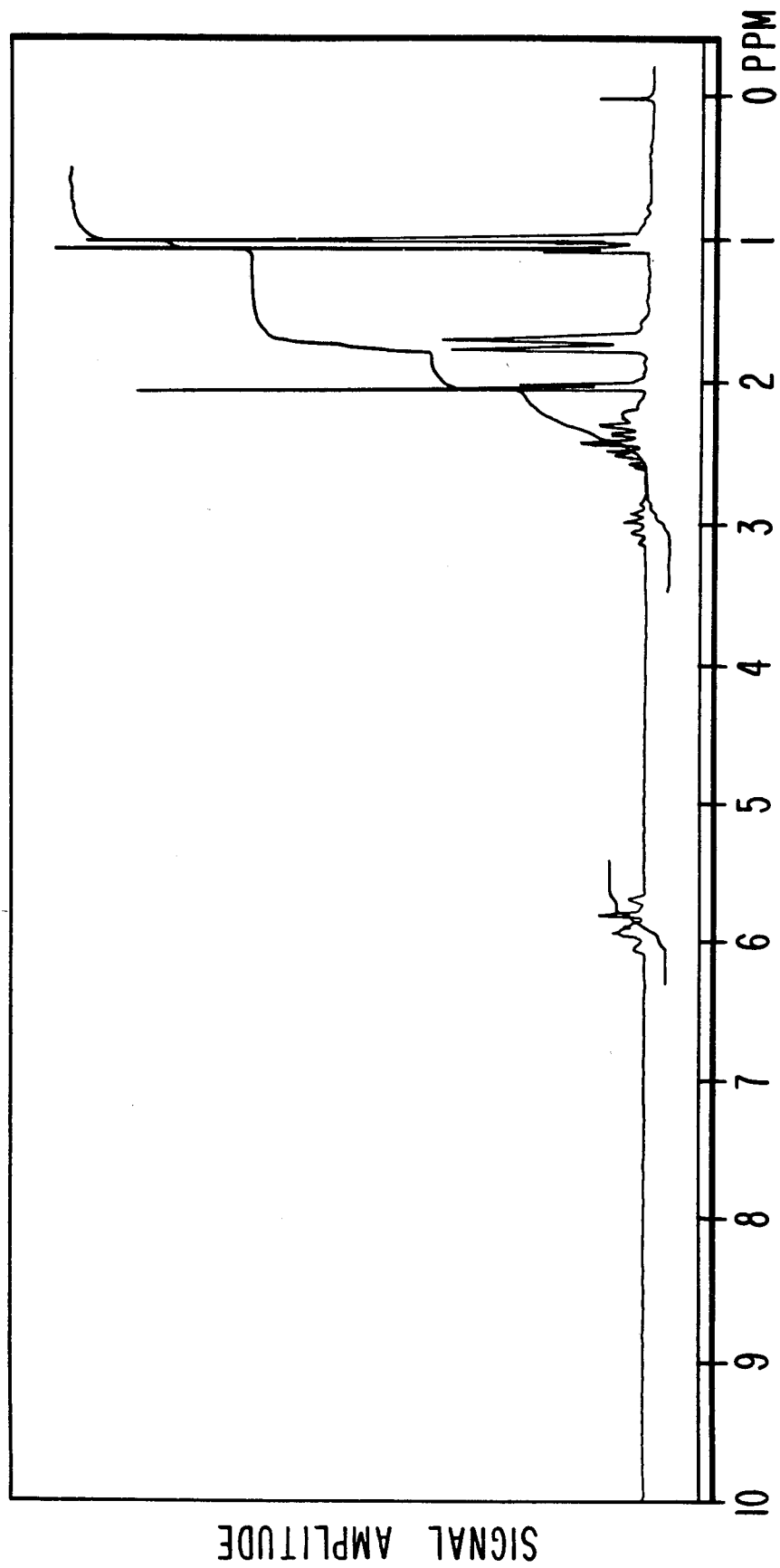

ISOSOLANONE AND SOLANONE INTERMEDIATES AND ORGANOLEPTIC USES

This is a divisional of application Ser. No. 542,477, filed 10/17/83, now U.S. Pat. No. 4,476,147 which, in turn, is a divisional of U.S. Pat. Ser. No. 380,542, filed 5/20/82, now U.S. Pat. No. 4,433,695, issued 2/28/84.

The novel process of our invention involves the steps of:

(i) formation of the compound having the structure:

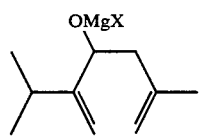

by means of reaction of the compound having the structure:

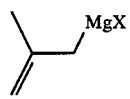

with the compound having the structure:

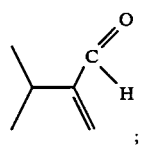

(ii) acid hydrolysis of the compound having the structure:

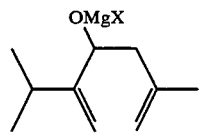

in order to form the compound having the structure:

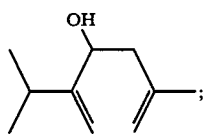

(iii) reaction of the compound having the structure:

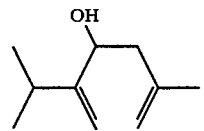

with the a member of the ketoester genus having the structure:

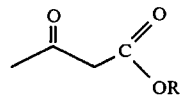

in order to form the ketoester having the structure:

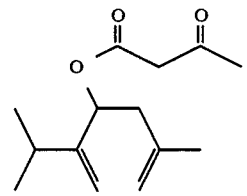

or in order to form, directly, the compound having the structure:

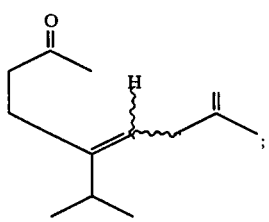

(iv) reacting the ketoester having the structure:

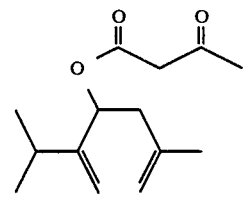

in the presence of an appropriate catalyst to form the compound having the structure:

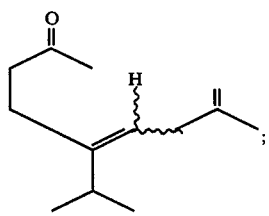

(v) isomerizing the compound having the structure:

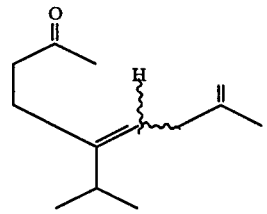

in order to form one or both of the compounds defined according to the structures:

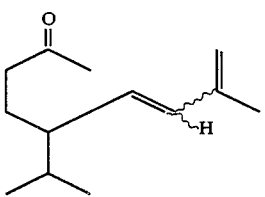

and/or

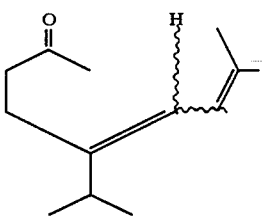

BACKGROUND OF THE INVENTION

Solanone is known as a useful tobacco flavorant and flavor enhancer. It is a mixture consisting primarily of the compounds defined according to the structure:

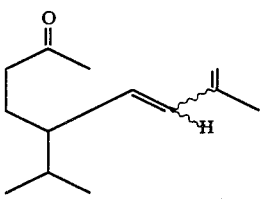

which is indicative of a cis and trans mixture of compounds having the structures:

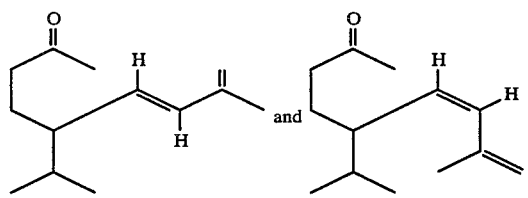

Isosolanone, an isomer of solanone, is a mixture of cis and trans isomers defined according to the structure:

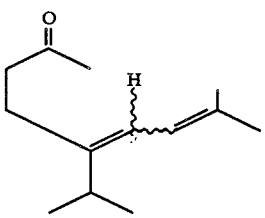

which is indicative of a mixture of cis and trans isomers having the structures:

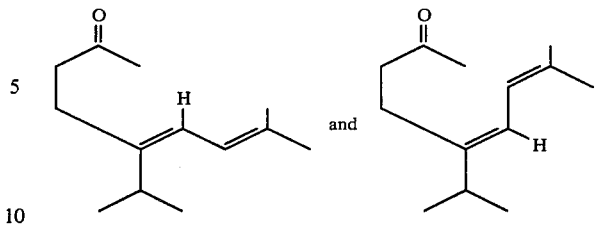

Isosolanone and solanone are disclosed in a paper by Demole and Berthet entitled "A Chemical Study of Burley Tobacco Flavour (Nicotiana tabacum L.) I. Volatile to medium-volatile constituents", Helvetica Chimica Acta, Volume 55, Fasc. 6(1972) Nr. 175–176, pages 1866–1882, to be present in burley tobacco aroma.

A need has arisen, however, to produce in an economical and efficient manner solanone and isosolanone. The paper by Johnson and Nicholson entitled "The Structure, Chemistry and Synthesis of Solanone, A New Anomalous Terpenoid Ketone from Tobacco" published in J. Org. Chem. 30(9), 2918–21 (1965) discloses a rather complex synthesis for solanone and isosolanone.

Furthermore, in the perfumery art there is a considerable need for constituents having minty, herbal, anisic, cedarleaf, and pennyroyal aroma nuances with floral and coriander-like undertones.

Such fragrance materials have a wide utilization in the presence of the perfumery compound of our invention. A limited amount of such materials that give rise to these properties is available from natural sources but the natural materials are subject to wide variations in quality, are expensive and are often in critically short supply.

In addition, there is a continuing search for food flavor compositions which can vary, fortify, modify, enhance, augment or otherwise improve the flavor and/or aroma of foodstuffs, medicinal products, toothpastes and chewing gums. To be satisfactory, such compositions should be stable, non-toxic and blendable with other ingredients to provide their own unique flavor and aroma nuances without detracting from the coingredients. Preferably such compositions should be naturally occurring or present in natural foodstuffs so that their ingestible safety can be readily recognized. These materials should be capable of being synthesized in a simple and economical manner. The need for safe flavors in the cooked vegetable flavor area and in the garlic area is well known. More specifically, there is a need for development of non-toxic materials which can replace natural materials not readily available having floral, patchouli-like, cooked red beet-like, earthy, garlic and green aroma and taste characteristics.

The instant invention provides the foregoing which the prior art has heretofore failed to provide. Furthermore, nothing in the prior art shows the unexpected, unobvious and advantageous value of the compounds having the structures:

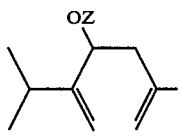

wherein Z represents hydrogen, MgX or:

and X represents chloro, bromo or iodo or of the compound defined according to the structure:

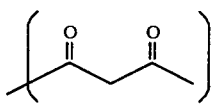

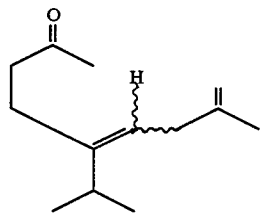

which is indicative of a mixture of cis and trans isomers having the structures:

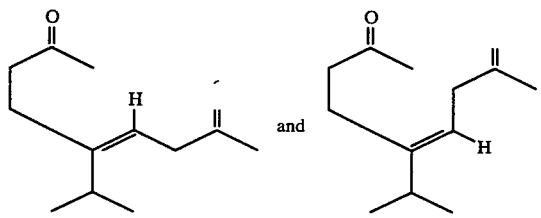

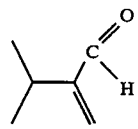

Figure 2:
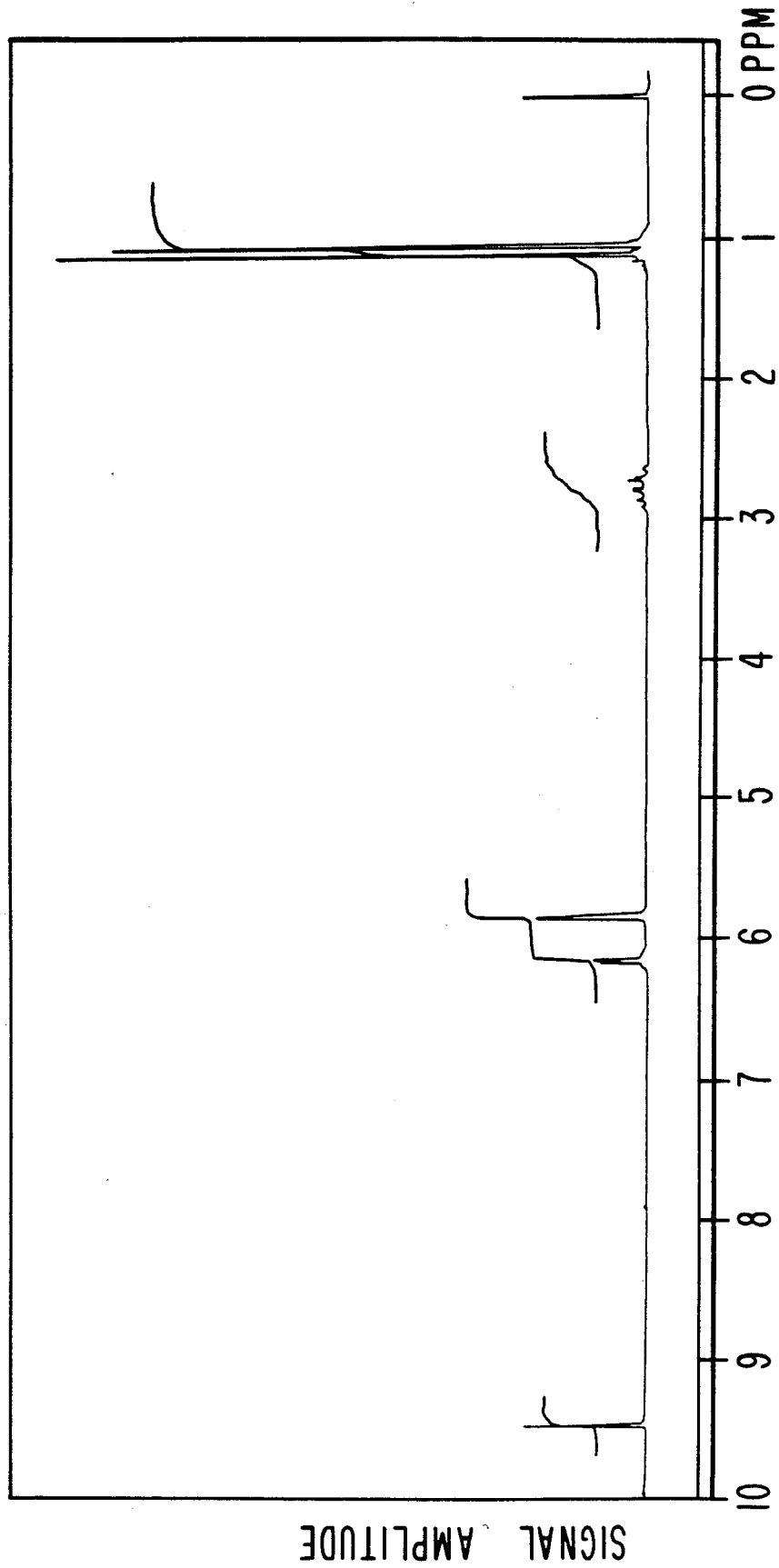

FIG. 2 is the NMR spectrum for fraction 2 of the distillation product of the reaction product of Example I containing the compound having the structure:

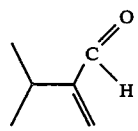

(Solvent: CFCl₃; Field strength: 100 MHz).

Figure 3:
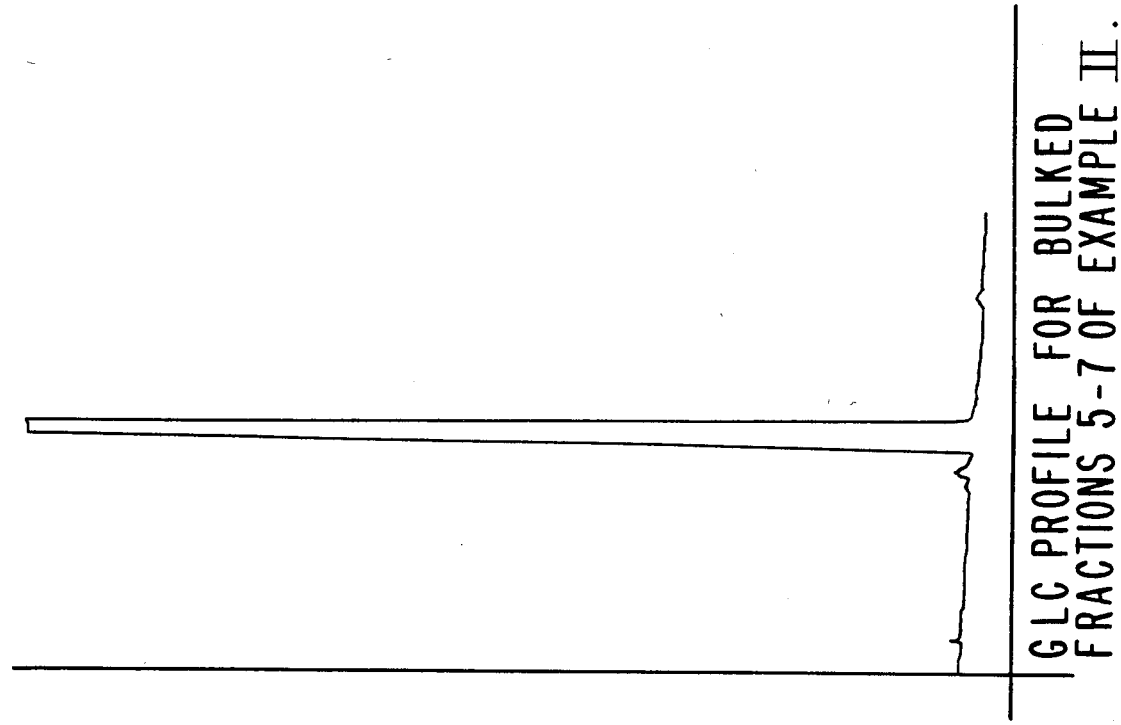

FIG. 3 is the GLC profile for bulked fractions 5-7 of the distillation product of the reaction product of Example II containing the compound having the structure:

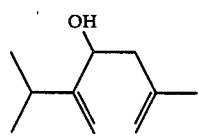

FIG. 4 is the NMR spectrum for fraction 3 of the distillation product of the reaction product of Example II containing the compound having the structure:

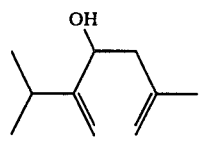

(Solvent: CFCl₃; Field Strength: 100 MHz).

FIG. 5 is the GLC profile for bulked fractions 7-11 of the distillation product of the reaction product of Example V(A) containing a mixture of cis and trans isomers of compounds defined according to the structure:

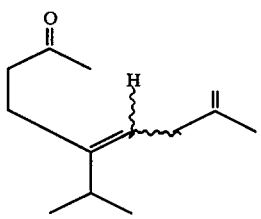

or defined according to the structures:

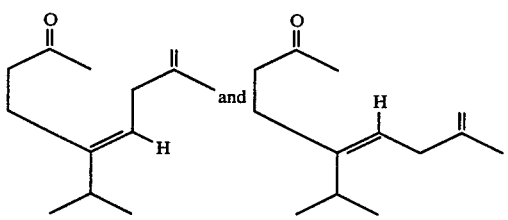

FIG. 6 is the GLC profile for the reaction product of Example VI(A) containing the cis and trans isomers of compounds defined according to the structure:

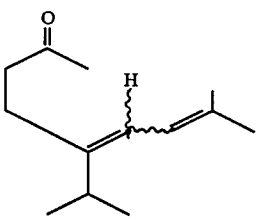

or according to the structures:

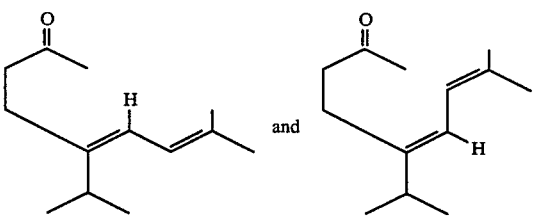

FIG. 7 is the NMR spectrum for the peak indicated by the reference numeral "61" of FIG. 6 for the cis or the trans isomer of the compounds defined according to the structure:

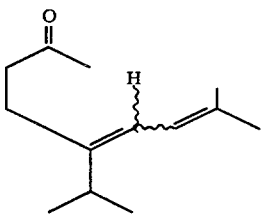

(Solvent: CFCl₃; Field strength: 100 MHz).

FIG. 8 is the NMR spectrum for the peak indicated by reference numeral "62" on FIG. 6 for the cis or the trans isomer of the compounds defined according to the structure:

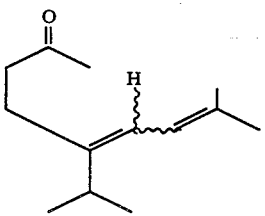

Figure 9:
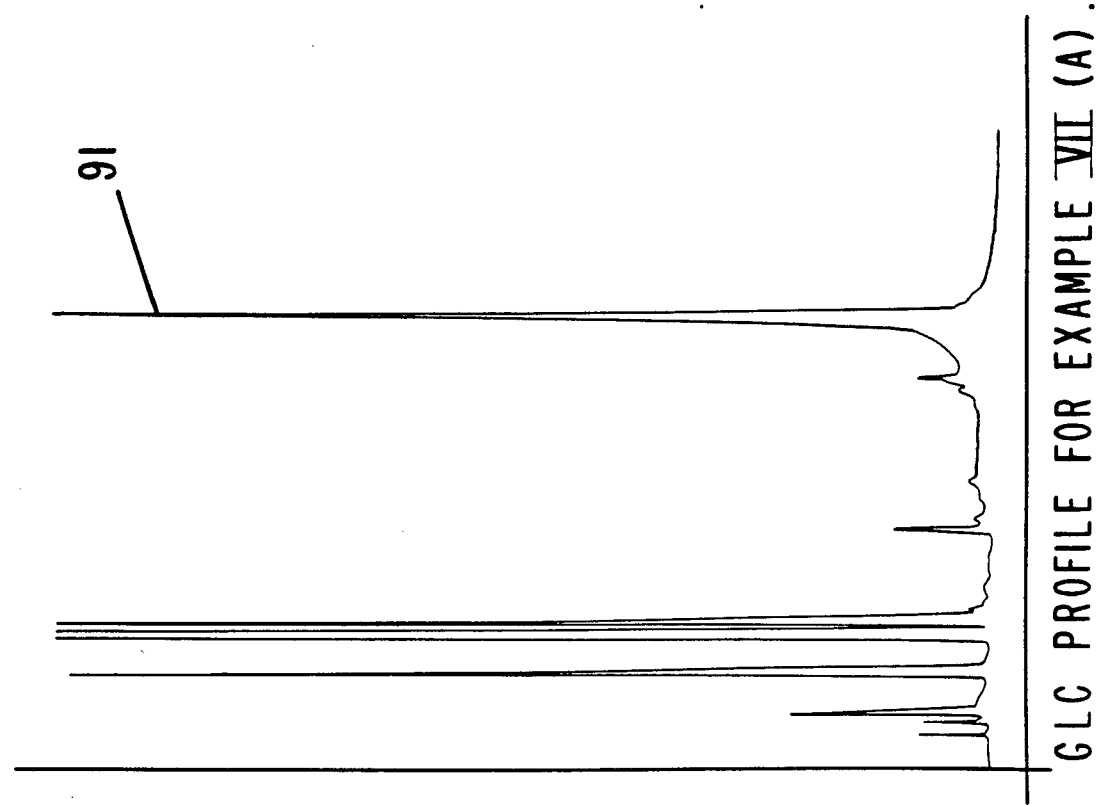

FIG. 9 is the GLC profile for the reaction product of Example VII(A) analyzed as a mixture containing the compounds having the structures:

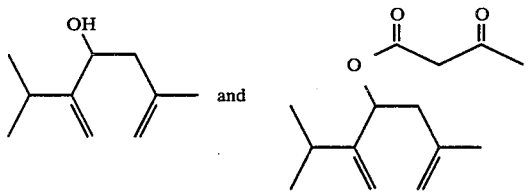

Figure 10:
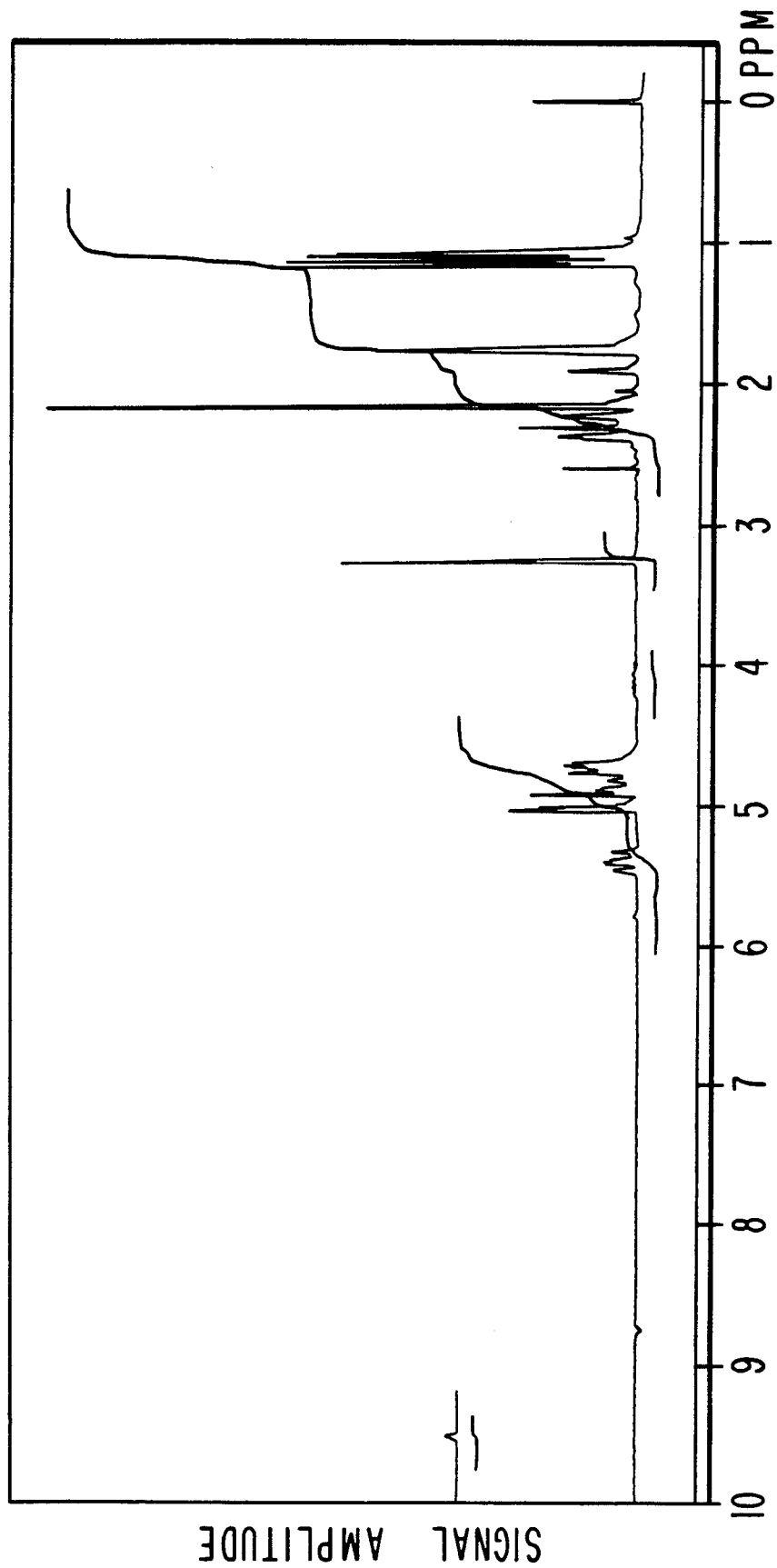

FIG. 10 is the NMR spectrum for the peak indicated by reference numeral "91" on FIG. 9; analyzed as a mixture of the compounds having the structures:

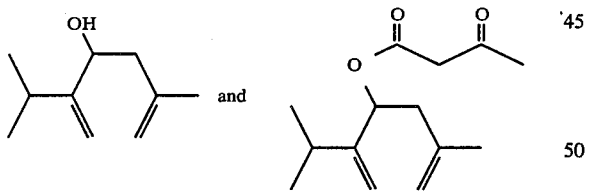

(Solvent: CFCl₃; Field strength: 100 MHz).

Figure 11:
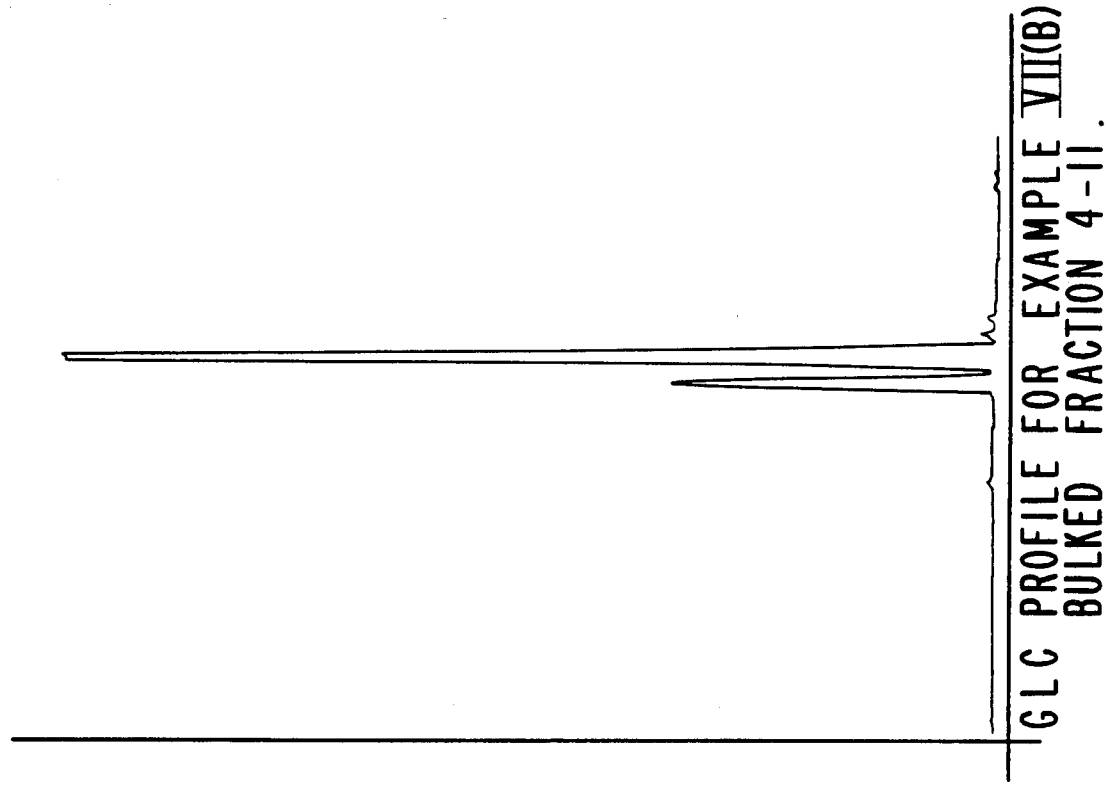

FIG. 11 is the GLC profile for bulked fractions 4-11 of the distillation product of the reaction product of Example VII(B) containing the compound having the structure:

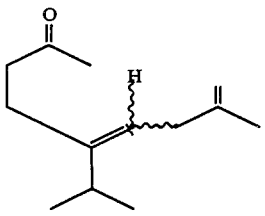

FIG. 12 is the NMR spectrum for the compound of fraction 7 of the distillation product of the reaction product of Example VII(B) containing the compound having the structure:

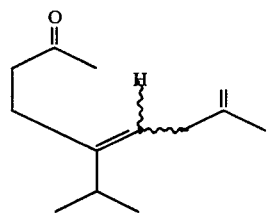

(Solvent: CFCl₃; Field strength: 100 MHz).

FIG. 13 is the infra-red spectrum for fraction 7 of the distillation product of the reaction product of Example VII(B) for a mixture of cis and trans isomers of the compounds defined according to the structure:

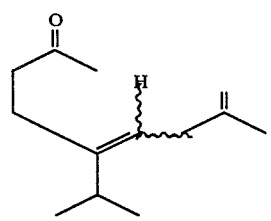

Figure 14:
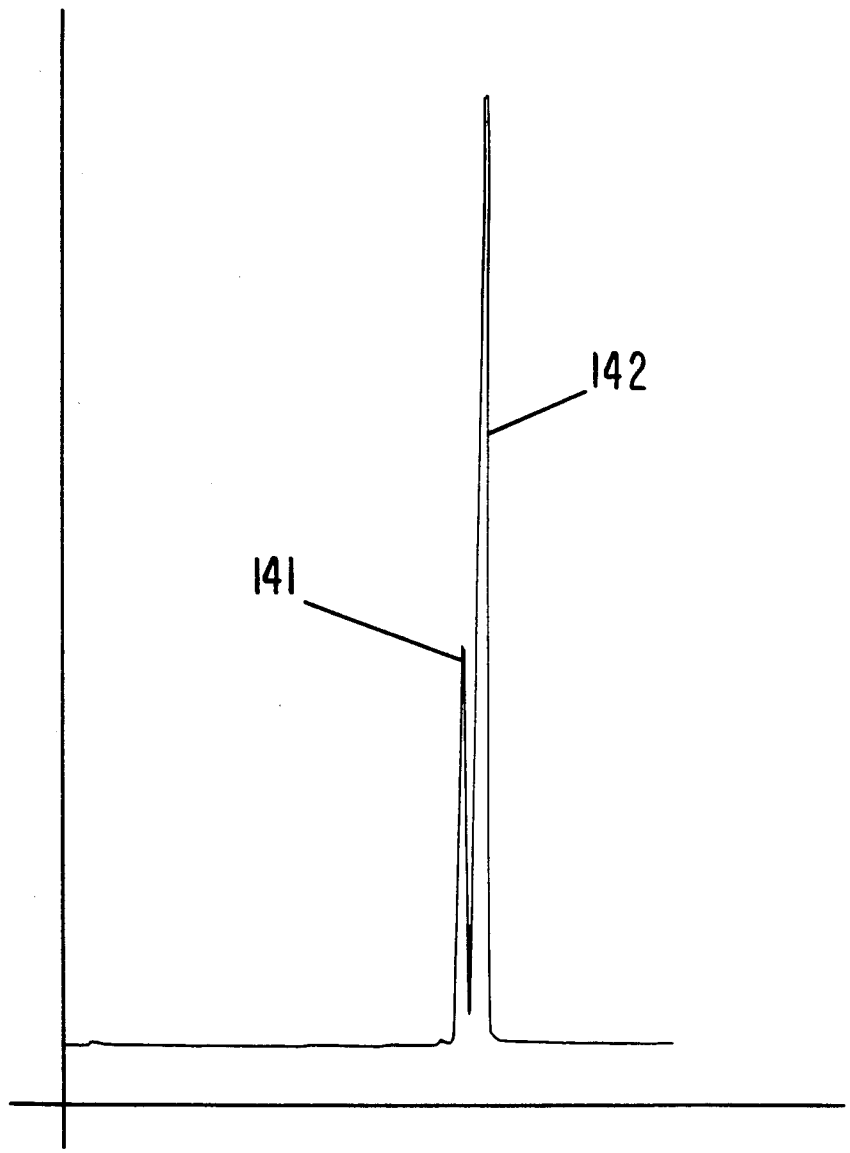

FIG. 14 is the GLC profile for bulked fractions 9-12 of the distillation product of the reaction product of Example IX containing a mixture of cis and trans isomers of the compounds defined according to the structure:

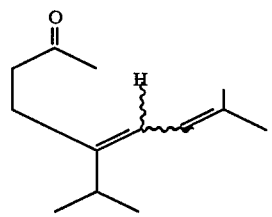

Figure 15:
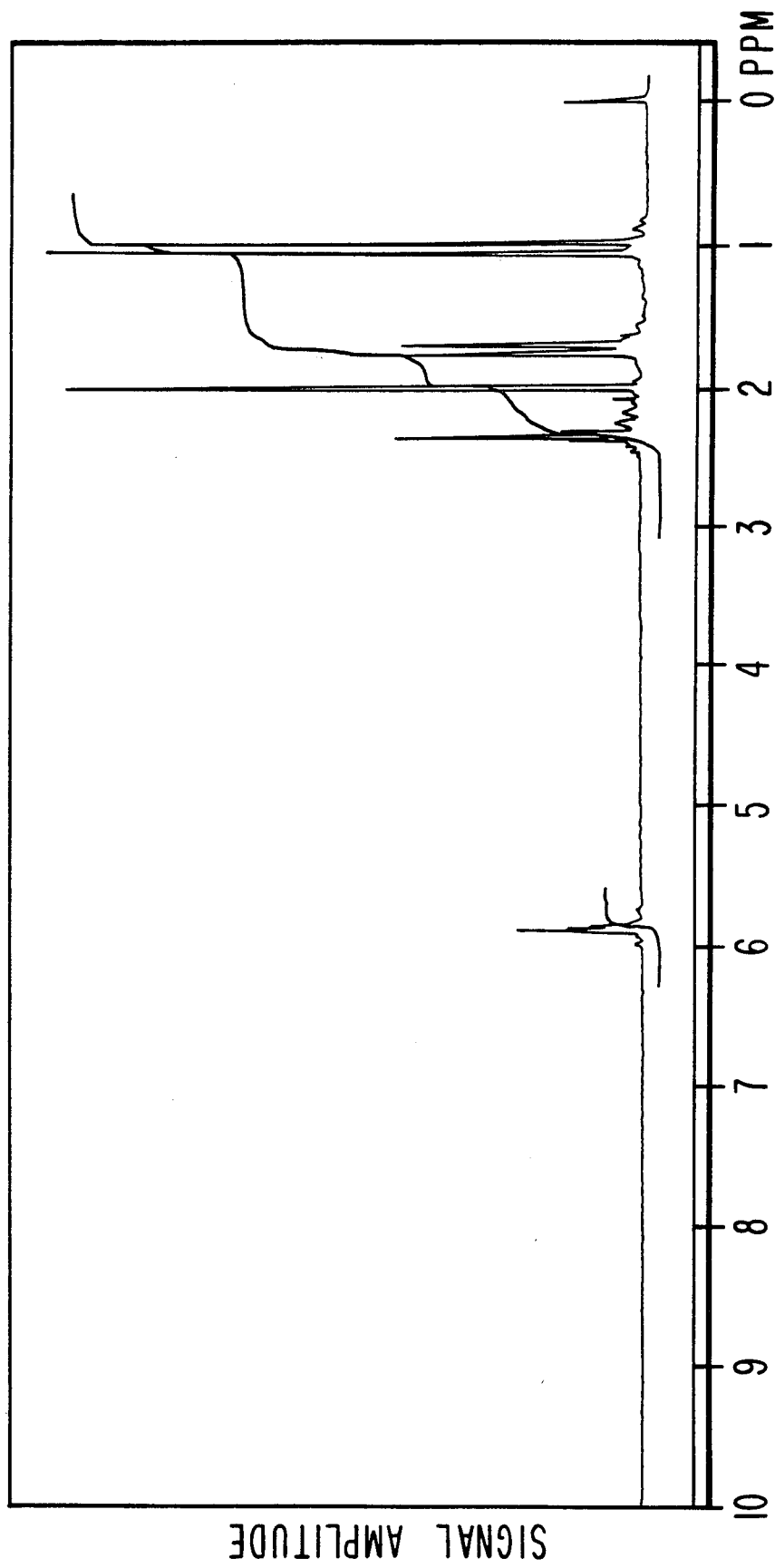

FIG. 15 is the NMR spectrum for the peak indicated by reference numeral "141" of FIG. 14 for the cis or trans isomer of the compounds defined according to the structure:

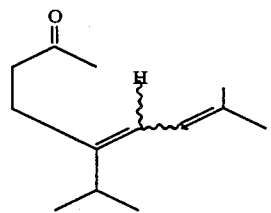

(Solvent: CFCl₃; Field strength: 100 MHz).

FIG. 16 is the NMR spectrum for the peak indicated by reference numeral "142" on FIG. 14 which is for the cis or trans isomer of the compounds defined according to the structure:

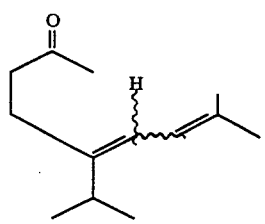

(Solvent: CFCl₃; Field strength: 100 MHz).

DETAILED DESCRIPTION OF THE DRAWINGS

In FIG. 6, the peaks indicated by reference numerals "61" and "62" are for the cis and trans isomers of the compounds defined according to the structure:

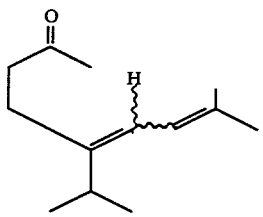

Thus, the peak indicated by reference numeral "61" is for the cis or trans isomer of the compounds defined according to the structure:

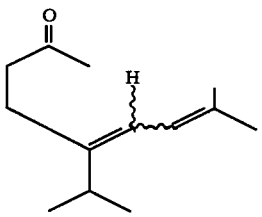

and the peak indicated by reference numeral "62" is for the cis or trans isomer of the compounds defined according to the structure:

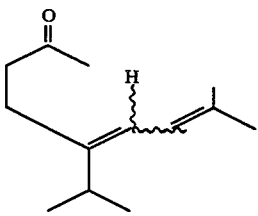

FIG. 9 is the GLC profile for the reaction product of Example VII(A). The peak indicated by reference numeral "91" is a peak analyzed as a mixture of compounds; the first compound having the structure:

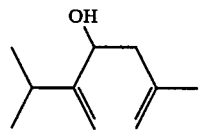

(approximately 15% of the mixture)

and the second compound having the structure:

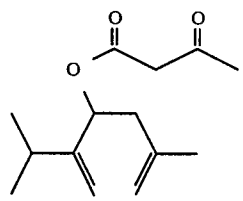

(approximately 85% of the mixture)

FIG. 14 is the GLC profile for bulked fractions 9-12 of the distillation product of the reaction product of Example IX (conditions: SE-30 column programmed at 100°-220° C. at 8° C. per minute) for the cis and trans isomer mixtures of compounds defined according to the structures:

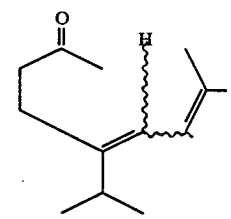

and

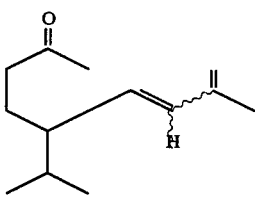

The peak indicated by reference numeral "141" is the peak for the cis or the trans isomer of the compounds having the structure:

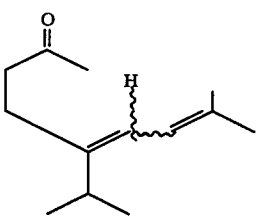

The peak indicated by the reference numeral "142" is for the cis or the trans isomer of the compounds having the structure:

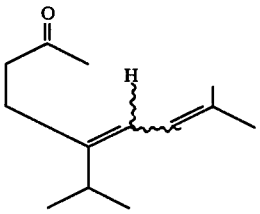

THE INVENTION

The present invention provides an efficient low cost process for producing isosolanone which is a mixture of cis and trans isomers defined according to the structure:

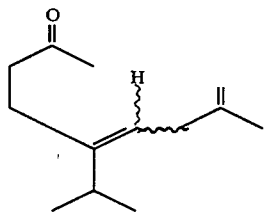

or shown by the structures:

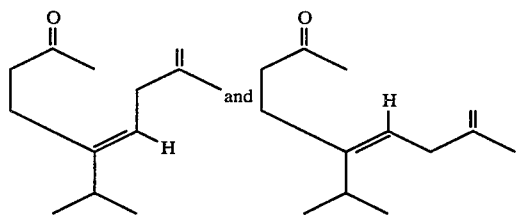

as well as solanone, a mixture of cis and trans isomers defined according to the structure:

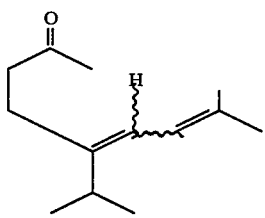

also shown by the structures:

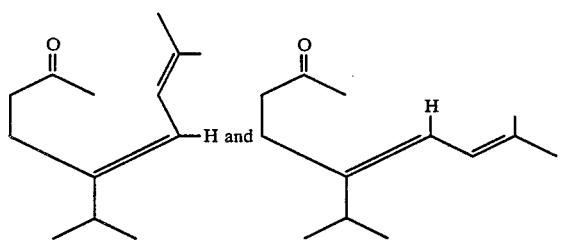

In addition, the present invention provides organoleptically useful intermediates resulting from the practice of said process. The organoleptically useful intermediates have the structures:

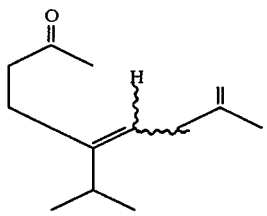

(sometimes referred to herein as "Structure 3")
(a mixture of cis and trans isomers also shown by the structures:

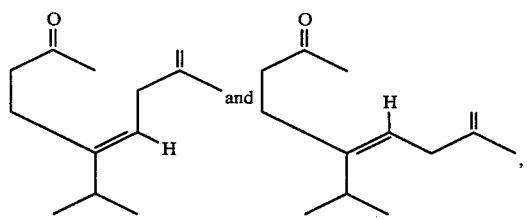

as well as:

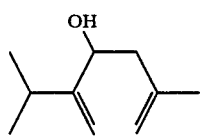

(sometimes referred to herein as "Structure 4").

The present invention also provides the genus of novel compounds which are defined according to the structure:

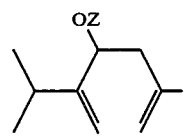

(sometimes referred to herein as "Structure 5") wherein Z represents hydrogen, MgX or the moiety having the structure:

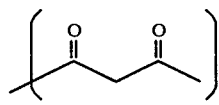

and wherein X represents chloro, bromo or iodo. When Z is hydrogen, the compound defined according to the structure:

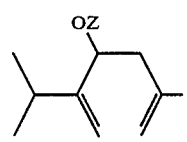

actually has the structure:

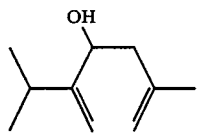

which is as stated supra useful for its organoleptic properties in addition to being useful as an intermediate in the production of solanone or isosolanone.

The compound having the structure:

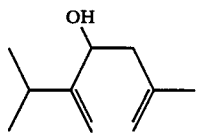

is capable of augmenting or enhancing red beet flavors and nuances that relate to same including patchouli-like and earthy aroma and taste nuances. This compound having the structure:

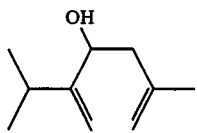

is also useful in augmenting or enhancing the minty, herbal, anisic, cedarleaf and pennyroyal-like aromas with floral and coriander undertones of perfumes, colognes and perfumed articles.

The mixture of cis and trans isomers of the compounds defined according to the structure:

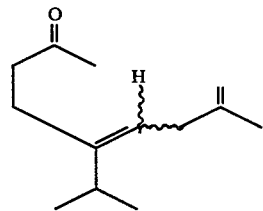

is useful for augmenting or enhancing the aroma or taste of alliaceous flavors, particularly garlic flavors, by augmenting or enhancing the garlic and green aroma and taste nuances of alliaceous-flavored foodstuffs.

The economic straightforward process of our invention may be described by the fllowing sequence of reactions:

Reaction I

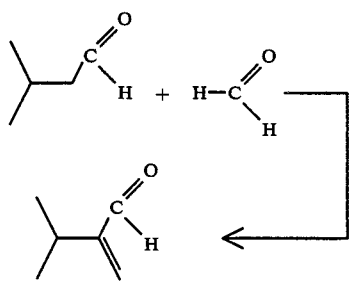

Reaction II

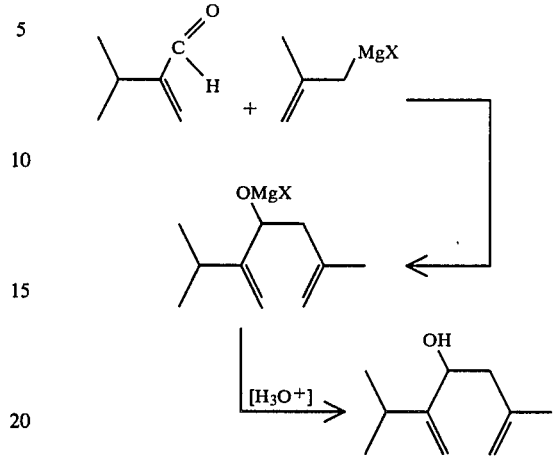

(wherein X represents chloro, bromo or iodo).

Reaction III

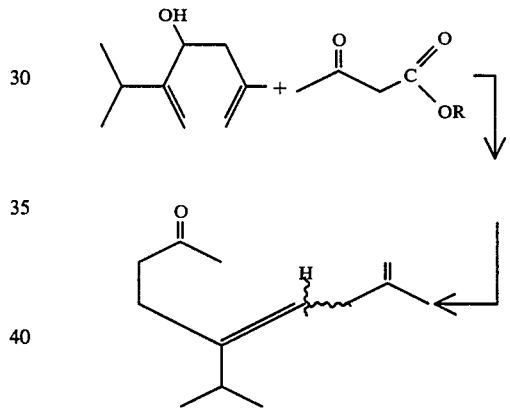

(in one step or via the intermediate:

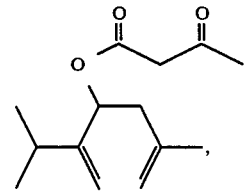

Reaction IV

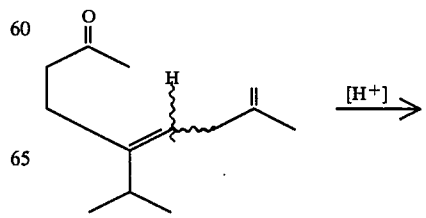

-continued

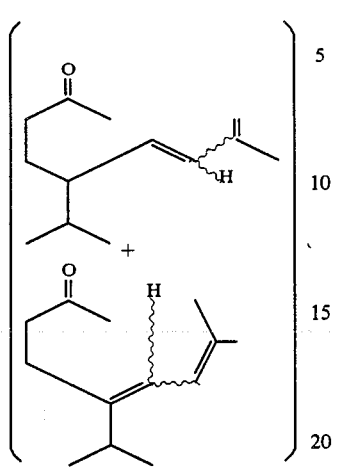

In carrying out Reaction I:

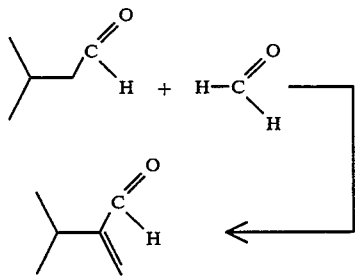

any secondary amine can be used as a catalyst. The formaldehyde source may be paraformaldehyde, formalin or trioxane but formalin is the preferred formaldehyde source. The reaction pressure may be atmospheric or super-atmospheric but atmospheric pressure is preferred. The reaction temperature range is from about 60° C. up to about 100° C. with a preferred range of 75°–80° C. In addition, Mannich-type reaction conditions using an amine salt catalyst or normal "aldol"-type conditions using sodium hydroxide or barium hydroxide may also be used. The isovaleraldehyde:formaldehyde mole ratio may vary from about 1:10 up to about 10:1 with a preferred range of mole ratio of isovaleraldehyde:formaldehyde being from 1:1 up to about 1:1.1. The mole ratio of isovaleraldehyde:catalyst may vary from about 1:1 down to about 1:0.01 with a preferred mole ratio of isovaleraldehyde: catalyst being from about 1:0.1 down to about 1:0.05.

With reference to the Reaction II sequence:

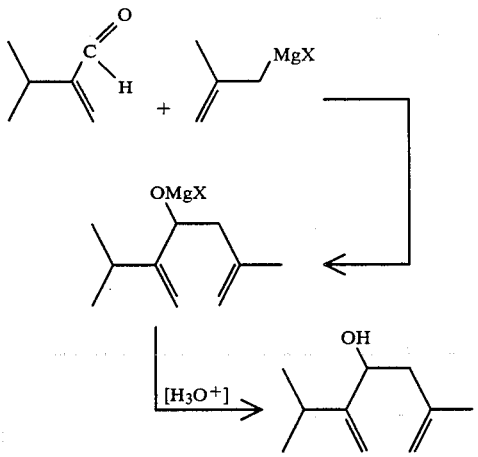

the mole ratio of 2-isopropylpropenal:methallyl halide (which becomes the methallyl Grignard reagent) may vary from about 1:1 to about 1:1.5 and the mole ratio of magnesium metal:methallyl halide may vary from about 0.1:1 up to about 1.5:1.

The methallyl halide reagent may be methallyl chloride, methallyl bromide or methallyl iodide with methallyl chloride being the preferred reagent. The reaction is carried out in a solvent which is inert to the reactants in the desired reaction temperature range (0° C. up to about 150° C.; at 1 up to about 100 atmospheres pressure). Thus, the solvent used may be diethylether, di-n-butylether, tetrahydrofuran, other ethers or mixtures of ethers and inert co-solvents (e.g. xylene, toluene or benzene). The preferred solvent is tetrahydrofuran. The hydrolysis may be carried out in the presence of any acid such as dilute hydrochloric acid, aqueous ammonium chloride, dilute sulfuric acid or dilute acetic acid.

The resulting compound having the structure:

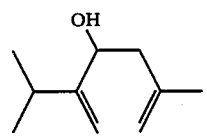

produced by hydrolysis of the compound having the structure:

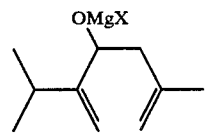

wherein X is chloro, bromo or iodo, may be carefully distilled (via fractional distillation) and used "as is" for its organoleptic properties in augmenting or enhancing the aroma or taste of perfume compositions, colognes, perfumed articles, foodstuffs, chewing gums, toothpastes, medicinal products or chewing tobaccos. In the alternative, the compound having the structure:

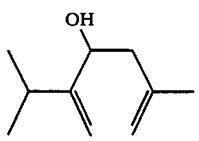

may be further reacted.

Thus, in the Reaction III:

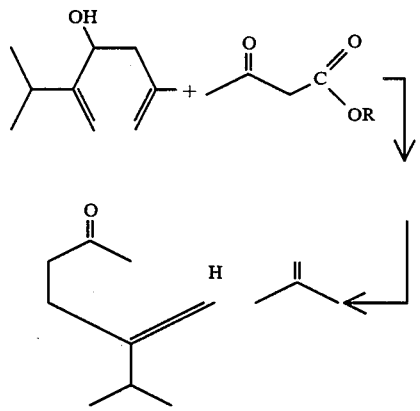

wherein R represents $C_1$-$C_4$ lower alkyl, methyl, ethyl, isopropyl, n-propyl, n-butyl, isobutyl or t-butyl, this reaction may take place in one step or it may take place in two steps forming an intermediate ketoester having the structure:

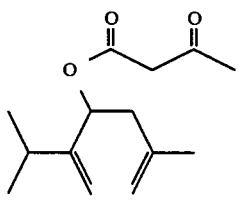

thusly:

Reaction IIIA:

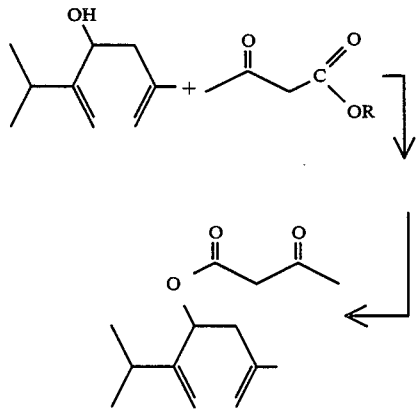

Reaction IIIB:

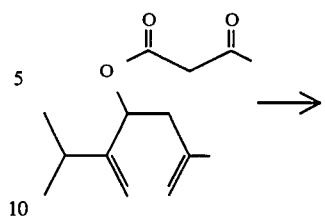

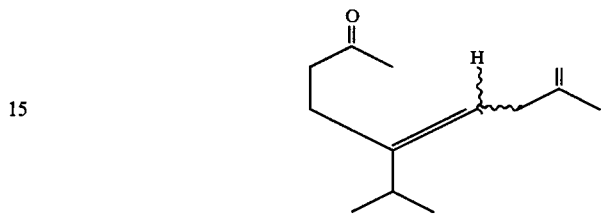

In carrying out Reaction IIIA,

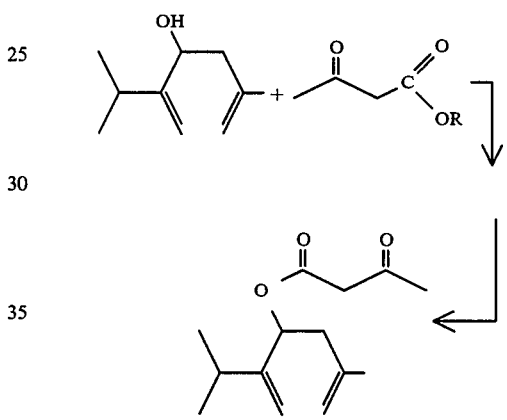

the catalyst used is aluminum triisopropylate. The mole ratio of alcohol 4:ketoester may vary from about 1:5 up to about 2:1. The mole ratio of alcohol 4:aluminum triisopropylate may vary from about 100:1 down to about 5:1. The co-solvent used may be any inert material which allows the desired temperature to be achieved such as toluene or xylene. A co-solvent is not necessary and the preferred process would not be used in conjunction with such a co-solvent. At the end of the reaction, the reaction product may be "worked-up" and distilled or the crude product may be used as is without distillation for further reaction to form the compound having the structure:

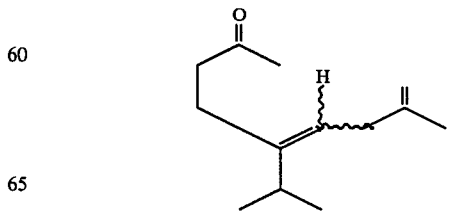

The preferred ketoester having the structure:

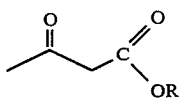

is methyl or ethyl acetoacetate.

In the Reaction IIIB:

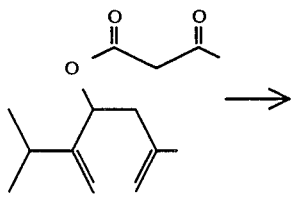

to form the mixture of cis and trans isomers of the compounds having the structure:

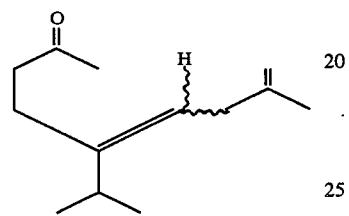

the catalyst used may be aluminum triisopropylate or sodium carbonate/polyethylene oxide. If aluminum isopropylate is used as a catalyst, either no solvent or a high boiling solvent (e.g. decalin) may be used. If sodium carbonate is used, then N-methyl-2-pyrrolidinone is the preferred solvent. The reaction temperature may vary from about 150° C. up to about 200° C. When using aluminum triisopropylate as a catalyst, the mole ratio of aluminum triisopropylate:ketoester having the structure:

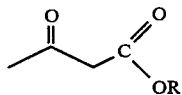

may vary from about 1:100 down to 1:5. When using sodium carbonate as a catalyst, the mole ratio of sodium carbonate:ketoester having the structure:

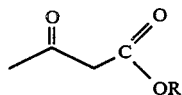

may vary from about 1:20 down to 1:2.

The resulting product may be "worked-up" and distilled as by fractional distillation particularly if it is desired to use the product "as is" for its organoleptic properties in augmenting or enhancing the taste of alliaceous-flavored foodstuffs. The resulting product may be used "crude" after stripping the solvent for the next reaction, however.

In carrying out the Reaction IV to form the mixtures of cis and trans isomers defined according to the structures:

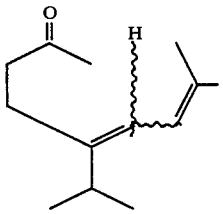

and

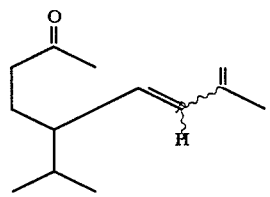

that is, the reaction:

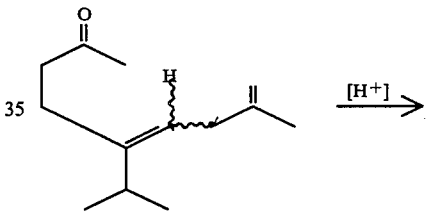

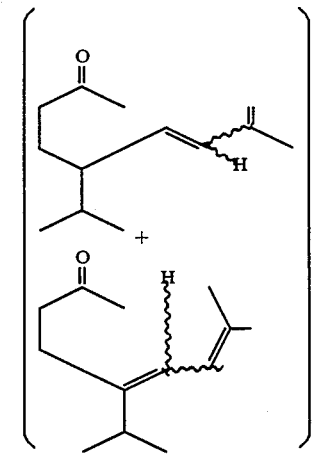

the catalyst used may be para-toluenesulfonic acid or any other strong mineral acid, e.g. phosphoric acid or sulfuric acid. Preferred is para-toluenesulfonic acid, however. The co-solvent used may be any suitably inert material which allows the achievement of the desired reaction temperature. Among such preferred solvents are toluene or xylene. The reaction temperature may be in the range of from about 40° C. up to about 150° C. The preferred reaction temperature range is from about 100° C. to about 120° C. in order to optimize the time of reaction and maximize the yield of product.

The mole ratio of protonic acid compound having the structure 3 may vary from about 1:100 down to 1:10. The weight ratio of solvent:compound having the structure 3 may vary from about 100:1 down to about 1:10 with a preferred weight ratio of solvent:compound having the structure 3 being 1:1. The resulting reaction product may be "worked-up" and fractionally distilled to yield individually compounds 1 and 2 or mixtures of both compounds (mixtures of cis and trans isomers) having the structures:

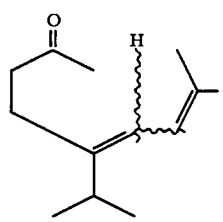
(1)

and

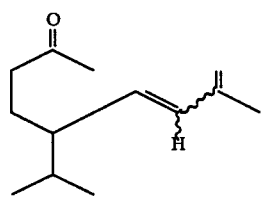
(2)

Each of these compounds 1 and 2 and mixtures containing both compounds have organoleptic uses in augmenting or enhancing the aroma or taste of consumable materials including foodstuffs, chewing gums, toothpastes, smoking tobaccos, medicinal products, perfumes, colognes, perfumed articles, (e.g. solid or liquid anionic, cationic, nonionic or zwitterionic detergents, perfumed polymers, hair preparations, cosmetic powders and the like), smoking tobacco products and smoking tobaccos.

The Reaction I:

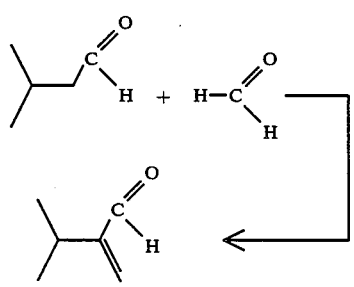

is basically described in the literature (Chem. Abstracts 93:238810j and 93:185765q).

In the Reaction sequence II:

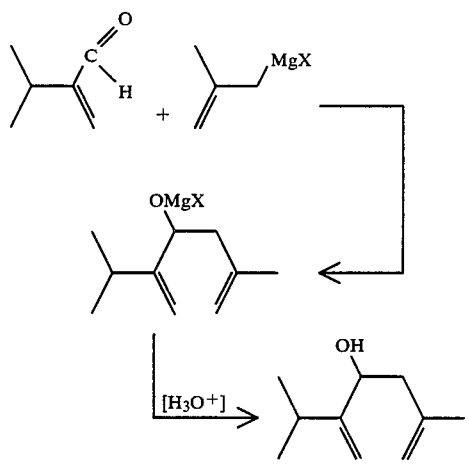

it is preferred that the compound having the structure:

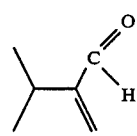

and methallyl chloride be added simultaneously to magnesium. The methallyl Grignard reagent is preferred to be formed in situ and is preferred to be consumed as rapidly as it is formed. This avoids or reduces the usual problems associated with allylic Grignards including lower yields due to coupling and need for high dilution and low temperature to avoid coupling when synthesizing the Grignard reagent.

In place of aluminum triisopropylate used as a catalyst in the Reaction IIIA:

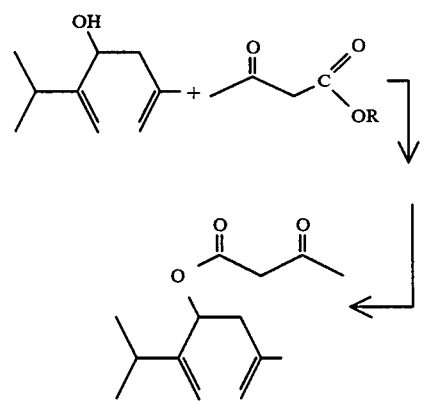

any mildly basic catalyst is usable, but the aluminum triisopropylate is the preferred catalyst. In the alternative, in place of using the ketoester having the structure:

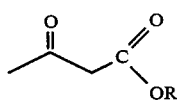

diketene may be used.

The Reaction sequences IIIA and IIIB:

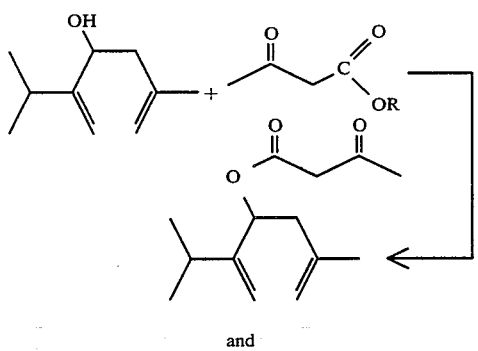

and

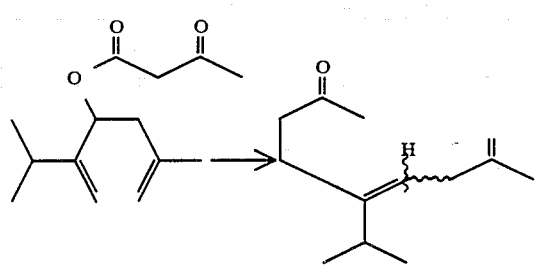

together constitute an example of the "Carrol reaction", and such a reaction is set forth in J.C.S., 1266(1940).

The Reaction IV:

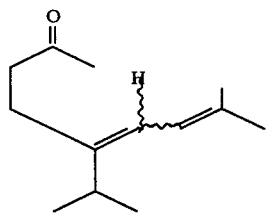

was previously reported using a para-toluenesulfonic acidethanol system. Under these conditions, the isosolanone forms a number of non-volatile materials which are antithetical to utility for their organoleptic properties. Using the para-toluenesulfonic acid-toluene or xylene system yields good isomerization to the cis and trans isosolanone defined according to the structure:

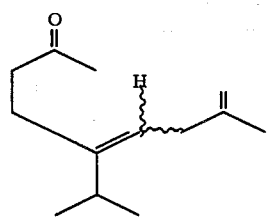

a highly desirable product useful for its organoleptic properties in augmenting or enhancing the aroma or taste of smoking tobacco or smoking tobacco articles or components of smoking tobacco articles such as the filter and the wrapper.

When one of the compounds:

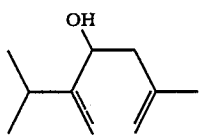

(mixture of cis or trans isomers) or (hereinafter collectively termed "oxo derivatives") are used taken alone or together as food flavor adjuvants, the nature of the co-ingredients included with said oxo compound(s) will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible nontoxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g. glycerine, and a flavoring composition which incorporates the oxo compound(s) of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g. sodium chloride; antioxidants, e.g. calcium and sodium ascorbate, ascorbic acid, butylated bydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan; cellulose and cellulose derivatives such as carboxymethyl cellulose and methyl cellulose; natural and synthetic gums such as gum arabic, gum tragacanth, gelatin, proteinaceous materials; lipids; carbohydrates; starches, pectins and emulsifiers, e.g. mono- and diglycerides of fatty acids, skim milk powder, hexoses, pentoses, disaccharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate, texturizers, anti-caking agents, e.g. aluminum calcium sulfate and tribasic calcium phosphate, enzymes; yeast foods, e.g. calcium lactate and calcium sulfate; nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid and 2-methyl-3-pentenoic acid; ketones and aldehydes, e.g. acetaldehyde, acetophenone, acetone, acetyl methyl carbinol, acrolein, n-butanal, crotonal, diacetyl, 2-methyl butanal, beta,-beta-dimethyl-acrolein, methyl-n-amyl ketone, n-hexenal, 2-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g. methyl sulfides and alkyl-alkenyl di- and trisulfides as set forth in U.S. Pat. No. 3,615,601 the specification for which is incorporated herein by reference, and other materials such as maltol, acetoin and acetals (e.g. 1,1-diethoxyethane, 1,1-dimethoxyethane and dimethoxymethane.

The specific flavoring adjuvant selected for use may be either solid or liquid depending upon the desired physical form of the ultimate product, i.e. foodstuff, whether simulated or natural, and should, in any event (i) be organoleptically compatible with the oxo compound(s) of our invention by not covering or spoiling the organoleptic properties (aroma and/or taste) thereof; (ii) be non-reactive with the oxo compound(s) of our invention and (iii) be capable of providing an environment in which the oxo compound(s) of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of the oxo compound(s) employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e. sufficient to alter, modify or enhance the organoleptic characteristics of the parent composition, whether foodstuff per se, chewing gum per se, medicinal product per se, toothpaste per se, or flavoring composition.

The use of insufficient quantities of the oxo compound(s) will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the oxo compound(s) ranging from a small but effective amount e.g. 0.05 parts per million up to about 100 parts per million based on total composition are suitable. Concentrations in excess of the maximum quantity stated are not normally recommended, since they fail to provide commensurate enhancement of organoleptic properties. In those instances wherein the oxo compound(s) is added to the foodstuff as an integral component of a flavoring composition, it is, of course, essential that the total quantity of flavoring composition employed be sufficient to yield an effective concentration of the oxo compound(s) in the foodstuff product.

Food flavoring compositions prepared in accordance with the present invention preferably contain the oxo compound(s) in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the oxo compound(s) with, for example, gum arabic, gum tragacanth, carrageenan and the like, and thereafter spray-drying the resultant mixture whereby to obtain the particular solid product. Pre-prepared flavor mixes in powder form, e.g. a fruit-flavored powder mix are obtained by mixing the dried solid components, e.g. starch, sugar and the like and the oxo commpound(s) in a dry blender until the requisite degree of uniformity is achieved.

It is presently preferred to combine with the oxo compound(s) of our invention, the following adjuvants:
p-Hydroxybenzyl acetone;
Geraniol;
Cassia oil;
Acetaldehyde;
Maltol;
Ethyl methyl phenyl glycidate;
Benzyl acetate;
Dimethyl sulfide;
Eugenol;
Vanillin;
Carryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
$\beta$-Damascone(1-crotonyl-2,2,6-trimethylcyclohex-1-ene);
$\beta$-Damascenone(1-crotonyl-2,2,6-trimethylcyclohexa-1,3-diene);
Beta-cyclohomocitral(2,2,6-trimethylcyclohex-1-ene carboxaldehyde);
Isoamyl butyrate;
Cis-3-hexenol-1;
2-Methyl-2-pentenoic acid;
Elemecine(4-allyl-1,2,6-trimethoxybenzene);
Isoelemecine(4-propenyl-1,2,6-trimethoxybenzene); and
2-(4-Hydroxy-4-methylpentyl)norbornadiene prepared according to U.S. Pat. No. 3,886,289 issued on May 27, 1975
Methyl(2-methyl propenyl)trisulfide;
Propenyl(2-methyl propenyl)trisulfide;
Ethyl(2-ethyl propenyl)trisulfide;
Methyl propenyl trisulfide;
Propyl propenyl trisulfide;
Methyl-propyl disulfide;
Methyl-propenyl disulfide;
Dipropyl-disulfide;
Propyl-propenyl disulfide;

Diallyl-disulfide;
Dimethyl-disulfide.

The compound having the structure:

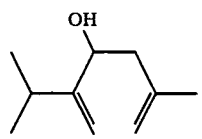

and one or more auxiliary perfume ingredients including, for example, alcohols (other than the compound having the structure):

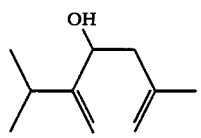

aldehydes, ketones, terpinic hydrocarbons, nitriles, esters, lactones, natural essential oils and synthetic essential oils may be admixed so that the combined odors of the individual components produce a pleasant and desired fragrance, particularly and preferably in floral fragrances. Such perfume compositions usually contain (a) the main note or the bouquet or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual component which contribute to their particular olfactory characteristics, however, the overall sensory effect of the perfume composition will be at least the sum total of the effects of each of the ingredients. Thus, the compound having the structure:

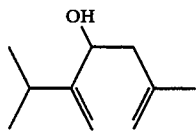

can be used to alter, modify or enhance the aroma characteristics of a perfume composition, for example, by utilizing or moderating the olfactory reaction contributed by another ingredient in the composition.

The amount of the compound having the structure:

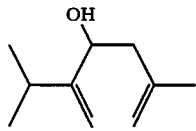

of our invention which will be effective in perfume compositions as well as in perfumed articles and colognes depends on many factors including the other ingredients, their amounts and the effects which are desired. It has been found that perfume compositions containing as little as 0.01% of the compound having the structure:

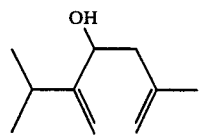

and as much as 50% of this compound can be used to impart a minty, herbal, anisic, cedarleaf, and pennyroyal-like aroma profile with floral and coriander-like undertones to perfume compositions, perfumed articles and colognes. The amount employed can range up to 70% of the fragrance components and will depend on considerations of cost, nature of the end product, the effect desired on the finished product and the particular fragrance sought.

The compound having the structure:

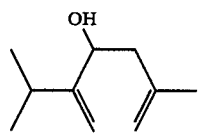

(taken alone or further together with other ingredients in perfume compositions) may be used as an olfactory component in solid or liquid anionic, cationic, nonionic or zwitterionic detergents and soaps, perfumed polymers such as perfumed polyethylene and perfumed polyurethanes, space odorants and deodorants, perfumes, colognes, toilet water, bath preparations such as creams, deodorants, hand lotions and sun screens, powders such as talcs, dusting powders, face powders and the like. When used as an olfactory component in perfumed articles, as little as 0.001% of the compound having the structure:

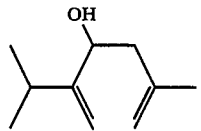

will suffice to impart an intense, minty, herbal, anisic, cedarleaf and pennyroyal-like aroma profile with coriander undertones to floral fragrance formulations including rose formulations. Generally, no more than 3% of the compound having the structure:

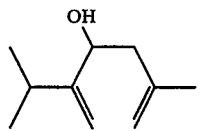

based on the ultimate end product is required. Thus, the range of use in perfumed articles of the compound having the structure:

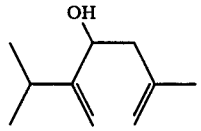

may vary from 0.001% up to 3% by weight of the perfumed article.

In addition, the perfume composition or fragrance composition of our invention can contain a vehicle or carrier for the compound having the structure:

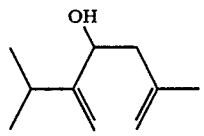

The vehicle can be a liquid such as a non-toxic alcohol, a non-toxic glycol or the like. An example of such a non-toxic alcohol is ethyl alcohol. Examples of such non-toxic glycols are 1,2-propylene glycol or 2,3-butylene glycol. The carrier can also be an absorbent solid such as a gum (e.g. gum arabic, xanthan gum, guar gum or mixtures of same) or components for encapsulating the composition, such as gelatin (as by coacervation) or a urea-formaldehyde prepolymer, where a polymer capsule wall is formed around a liquid perfume composition center.

Furthermore, the compounds defined according to the structures:

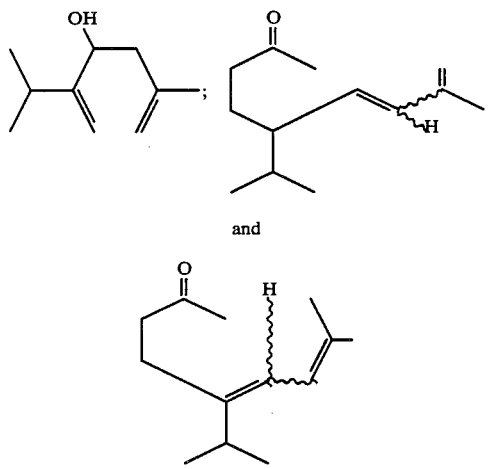

and produced according to the process of our invention are capable of supplying or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substituents or tobacco flavor formulations or augmenting the existing flavor characteristics where a natural flavor is deficient in some regard or supplementing the existing flavor impression to modify its quality, character or taste".

As used herein, the term "enhance" is intended to mean the intensification (without change in kind of quality of aroma or taste) of one of more taste and/or aroma nuances present in the organoleptic impression of tobacco or a tobacco substitute or a tobacco flavor.

Our invention thus provides an organoleptically improved smoking tobacco product and additives therefor, as well as methods of making same which overcome specific problems heretofore encountered in which specific desired musty, oily, slightly green, heavy, full-bodied burley tobacco character are created or enhanced and may be readily controlled and maintained at the desired uniform level regardless of variations in the tobacco components of the blend.

This invention further provides improved tobacco additives and methods whereby various musty, oily, slightly green, tobacco-like, full-bodied burley tobacco aroma and taste notes may be imparted to smoking tobacco products and may be readily varied and controlled to produce the desired uniform flavor characteristics.

In carrying out this aspect of our invention, we add to smoking tobacco materials or a suitable substitute therefor (e.g. dried lettuce leaves) an aroma and flavor additive containing as an active ingredient the 5-isopropyl-8-methyl-5,7-nonadien-2-one cis and trans isomer mix defined according to the structure:

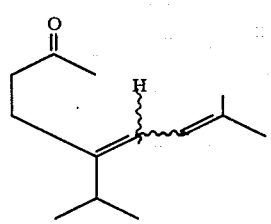

of our invention. In addition to the mixture of cis and trans isomers of the compounds defined according to the structure:

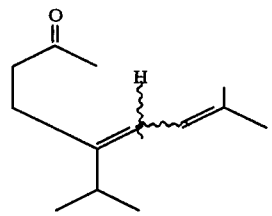

other flavor and aroma additives may be added to the smoking tobacco materials or substitute therefor either separately or in admixture with the cis and trans isomers of the compounds defined according to the structure:

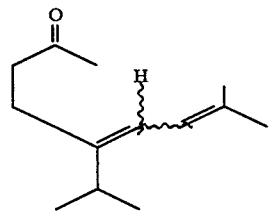

as follows:
(i) Synthetic materials:
  Beta-ethyl-cinnamaldehyde;
  Beta-cyclohomocitral;
  Eugenol;
  Dipentene;
  Beta-damascenone;
  Beta-damascone;
  Alpha-damascone;
  Gamma-damascone;
  Trans,trans delta-damascone produced according to U.S. Pat. No. 4,211,242

Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2,6-Dimethyl-2,6-undecadiene-10-one;
2-Methyl-5-isopropyl acetophenone;
2-Hydroxy-2,5,5,8a-tetramethyl-1-(2-hydroxy-ethyl)-decahydronaphthalene;
Dodecahydro-3a,6,6,9a-tetramethylnaphtho[2,1,b]furan;
4-Hydroxy hexanoic acid, gamma lactone; and
Polyisoprenoid hydrocarbons defined in Example V of U.S. Pat. No. 3,589,372 issued on June 29, 1971.

(ii) Natural oils:
Celery seed oil;
Coffee extract;
Bergamot oil;
Cocoa extract;
Nutmeg oil;
Origanum oil.

An aroma and flavoring concentrate containing a mixture of cis and trans isomers of the compounds defined according to the structure:

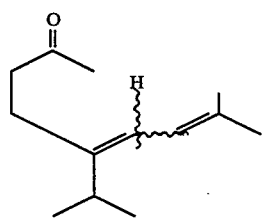

or a composition containing a mixture of the compounds defined according to the structure:

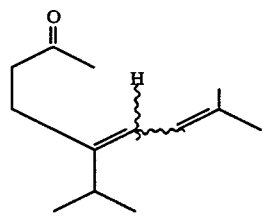

with a mixture of cis and trans isomers having the structures:

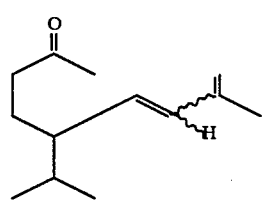

and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of natural and/or rich burley notes, we have found that satisfactory results are obtained if the proportion by weight of the sum total of the composition containing a mixture of cis and trans isomers of the compounds having the structure:

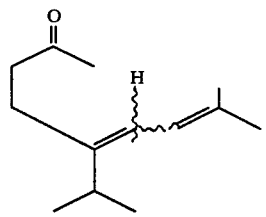

to smoking tobacco material is between 150 ppm and 1,500 ppm (0.015%–0.15%) of the active ingredients to the smoking tobacco material. We have further found that satisfactory results are obtained if the proportion by weight of the mixture of cis and trans isomers of the compounds having the structure:

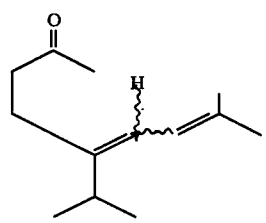

to additional flavoring material in the flavor composition is between 1,500 and 15,000 ppm (0.15%–1.5%).

Any convenient method for incorporating the mixture of cis and trans isomers of the compounds defined according to the structure:

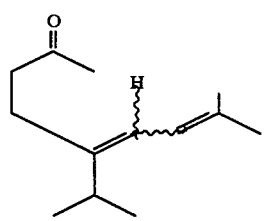

in the tobacco product may be employed. Thus the mixture of cis and trans isomers of the compounds defined according to the structure:

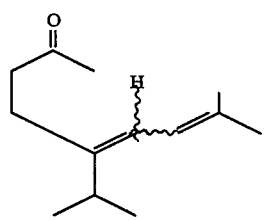

or the mixtures of cis and trans isomers containing the compounds having the structures:

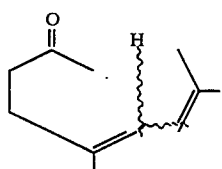

and

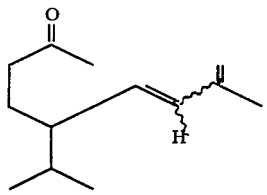

taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of the mixture of cis and trans isomers of the compound having the structure:

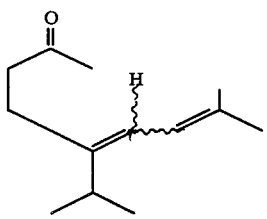

taken alone or taken together with other flavoring additives as set forth above may be applied by means of a suitable applicator such as a brush or roller on the paper or leaf wrapper for the smoking product or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the compound having the structure:

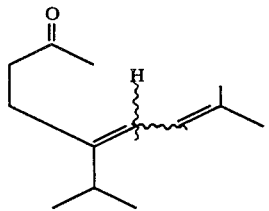

in excess of the amounts of concentrations above indicated so that when blended with other tobaccos, the final product will have the percentage within the indicated range.

In accordance with one specific example of our invention, an aged, cured and shredded domestic Virginia tobacco is sprayed with a 20% ethanol solution of the compound having the structure:

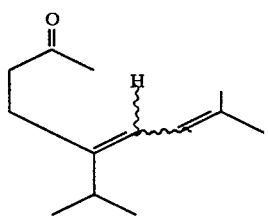

in an amount to provide a tobacco composition containing 400 ppm by weight of the compound having the structure:

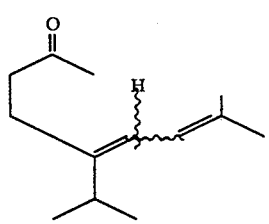

on a dry basis. Thereafter the alcohol is removed by evaporation and the tobacco is manufactured into cigarettes by the usual techniques. The cigarette, when treated as indicated, has a desired and pleasing aroma (increased smoke body sensation in the mouth with enhanced rich burley tobacco-like notes and pleasant aromatic nuances) which is detectable in the main and the side streams when the cigarette is smoked. This aroma is described as having musty, oily, slightly green, burley tobacco-like, full-bodied burley tobacco notes.

While our invention is particularly useful in the manufacture of smoking tobacco such as cigarette tobacco, cigar tobacco and pipe tobacco, other tobacco products formed from sheeted tobacco dust or fines may also be used. Likewise the compound having the structure:

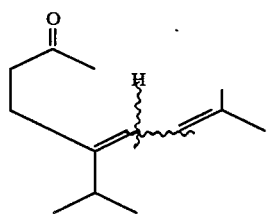

can be incorporated with materials such as filter tip materials, seam paste, packaging materials and the like which are used along with tobacco to form a product adapted for smoking. Furthermore, the compound having the structure:

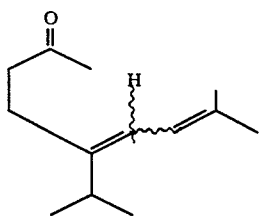

can be added to certain tobacco substitutes of natural or synthetic origins (e.g. dried lettuce leaves) and, accordingly, by the term "tobacco" as used throughout this specification, is meant any composition intended for human consumption by smoking or otherwise, whether composed of tobacco plant parts or substitute materials, or both.

The following Examples I-IX serve to illustrate the synthetic process of our invention. The examples following Example IX serve to illustrate that aspect of our invention concerning the organoleptic utilities of the products produced according to the process of our invention. The invention is to be considered to be restricted thereto only as indicated in the appended claims, however. All parts and percentages given herein are by weight unless otherwise specified.

EXAMPLE I

PREPARATION OF 2-ISOPROPYLACROLEIN

Reaction:

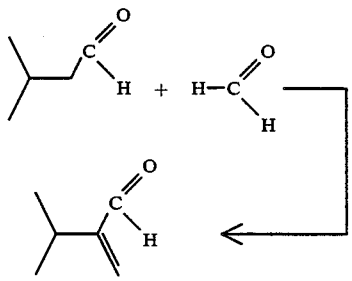

Into a 3-liter reaction flask equipped with thermometer, reflux condenser, heating mantle and stirrer is placed 860 grams (10 moles) of isovaleraldehyde. Over a period of thirty minutes, 65 grams (0.5 moles) of di-n-butylamine is added. The reaction mass exotherms to 48° C. and, with stirring, the reaction mass is heated to reflux at 85° C. While refluxing over a period of 90 minutes while maintaining the temperature of 83°–86° C. 900 grams (11.0 moles) of formaldehyde is added to the reaction mass. At the end of the addition of the formaldehyde, the reaction mass is refluxed for a period of 60 minutes. At the end of the 60 minute period, the organic layer is washed with dilute hydrochloric acid, water, saturated sodium carbonate solution, and saturated salt solution.

The crude material is then distilled through a 12" Goodloe column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 20/37 | 40/42 | 100 | 183 |
| 2 | 37 | 44 | 100 | 165 |

-continued

| Fraction Number | Vapor Temp. (°C.) | Liquid Temp. (°C.) | Pressure mm/Hg. | Weight of Fraction (grams) |
| --- | --- | --- | --- | --- |
| 3 | 40 | 52 | 100 | 180 |
| 4 | 30 | 150 | 100 | 213 |
| 5 | 90 | 210 | 3 | 88 |

Figure 1:
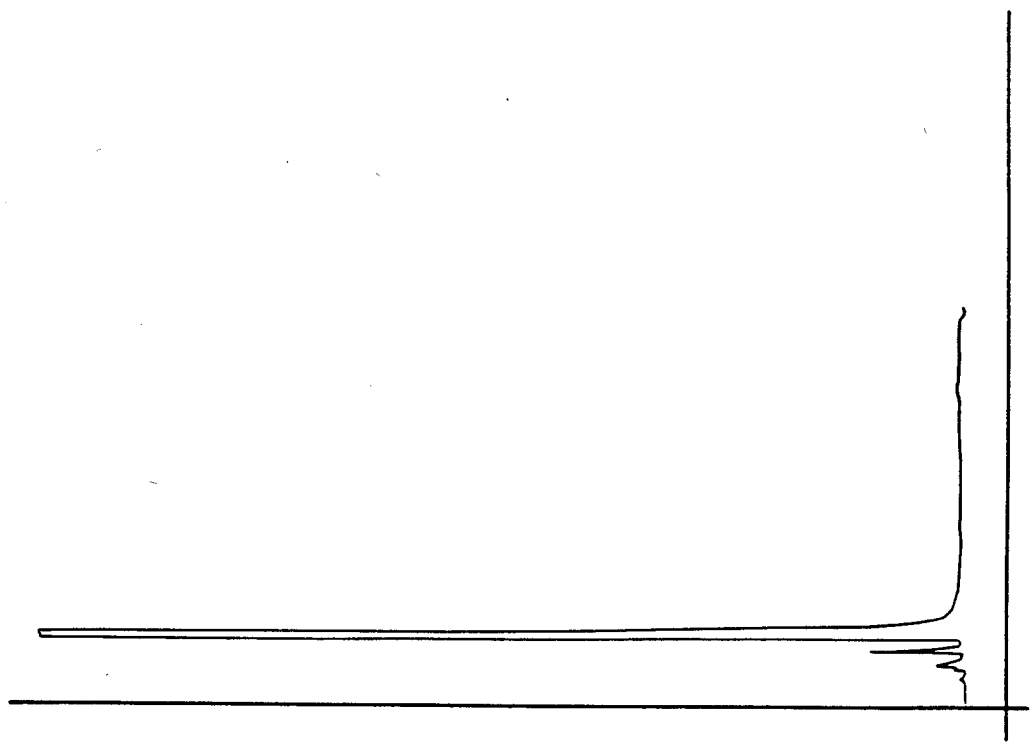
FIG. 1 is the GLC profile for bulked fractions 1-4 of the distillation product of the reaction product of Example I containing the compound having the structure.

FIG. 1 is the GLC profile for bulked fractions 1-4 of the foregoing distillation (Carbowax column programmed at 100°–220° C. at 8° C. per minute).

FIG. 2 is the NMR spectrum for fraction 2 of the foregoing distillation (Solvent: CFCl₃; Field strength: 100 MHz).

The NMR spectrum is for the compound having the structure:

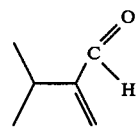

EXAMPLE II

PREPARATION OF 2,6-DIMETHYL-5-METHYLENE-1-HEPTEN-4-OL

Reaction:

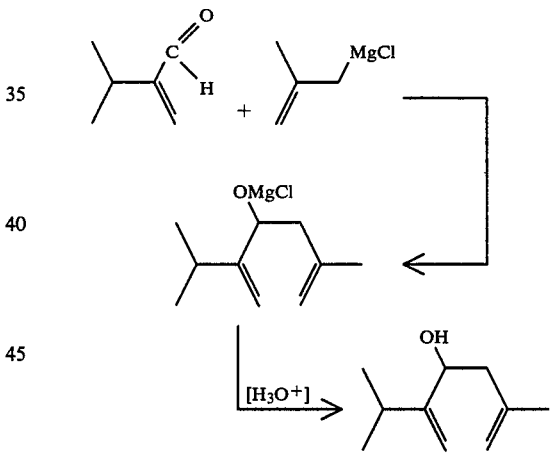

A mixture of magnesium turnings (146 grams) and tetrahydrofuran (2,000 grams) is heated to reflux with vigorous agitation. To this mixture is added a mixture of 3-chloro-2-methylpropene (500 grams), toluene (75 grams), and 3-methyl-2-methylenebutanal (500 grams prepared according to Example I), at such a rate as to maintain reflux. The addition requires approximately four hours. The mass is stirred at reflux for 30 minutes and is then cooled to room temperature and quenched into excess ice cold 10% aqueous acetic acid mixture. The organic layer is washed successively with an equal volume of water, saturated sodium carbonate solution and saturated salt solution. Rapid distillation at 3–12 mm/Hg pressure using a short column followed by careful redistillation (after bulking) through a 12"×1" Goodloe packed column yields 580 grams of 2,6-dimethyl-5-methylene-1-hepten-4-ol, boiling point range 73°–78° C. at 9 mm/Hg pressure.

The fractions yielded as a result of the short column distillation are as follows:

| Fraction Number | Vapor Temp. (°C.) | Liquid Temp. (°C.) | Pressure mm/Hg. | Weight of Fraction (grams) |
|---|---|---|---|---|
| 1 | 70/75 | 82/79 | 12/9 | 184 |
| 2 | 77 | 82 | 9.0 | 192 |
| 3 | 76 | 87 | 9.0 | 154 |
| 4 | 69 | 116 | 5.0 | 81 |
| 5 | 148 | 210 | 3.4 | 52 |

The fractions resulting from the total bulking and redistillation through the 12" Goodloe column are as follows:

| Fraction Number | Vapor Vapor (°C.) | Liquid Liquid (°C.) | Pressure mm/Hg. | Reflux Ratio | Weight of Fraction (grams) |
|---|---|---|---|---|---|
| 1 | 57/73 | 77/78 | 9/9 | 9:1 | 59 |
| 2 | 74 | 78 | 9 | 9:1 | 78 |
| 3 | 74 | 78 | 9 | 9:1 | 81 |
| 4 | 74 | 78 | 9 | 9:1 | 37 |
| 5 | 74 | 80 | 9 | 9:1 | 82 |
| 6 | 74 | 80 | 9 | 9:1 | 31 |
| 7 | 74 | 81 | 9 | 9:1 | 85 |
| 8 | 74 | 95 | 8.5 | 9:1 | 82 |
| 9 | 78 | 168 | 9 | 9:1 | 74 |
| 10 | 50 | 210 | 3 | 9:1 | 11 |

FIG. 3 is the GLC profile for bulked fractions 5–7 of the foregoing Goodloe distillation (conditions: SE-30 column programmed at 100°–220° C.).

FIG. 4 is the NMR spectrum for fraction 3 of the foregoing Goodloe distillation consisting essentially of the compound defined according to the structure:

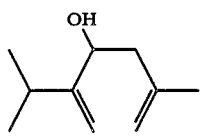

(Solvent: CFCl₃; Field strength: 100 MHz).

EXAMPLE III

LARGE SCALE PREPARATION OF 2,6-DIMETHYL-5-METHYLENE-1-HEPTEN-4-OL

Reaction:

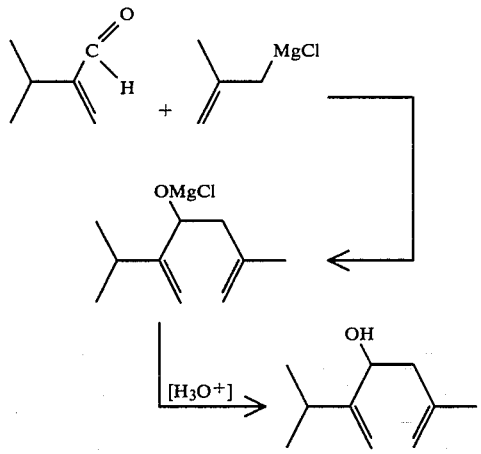

A mixture of magnesium turnings (406 grams) and tetrahydrofuran (1,450 grams) is heated to reflux and activated by the addition of a small amount of VITRIDE ®.

A mixture of 1,450 grams of 3-methyl-2-methylenebutanal (produced according to Example I) and 1,450 grams of methallyl chloride is added over a four hour period at reflux. The mixture is stirred at reflux for one hour and then is cooled to room temperature. The resulting mixture is poured slowly into approximately 3 kg of ice cold 50% acetic acid solution. The organic layer is washed once with dilute acetic acid. The total aqueous layer is then extracted with toluene. The combined organic layers are then washed successively with water and with saturated sodium bicarbonate solution. The solvent is recovered and the product is distilled rapidly using a short column to give 1,457 grams of material which GLC analysis shows contains 89.1% of 2,6-dimethyl-5-methylene-1-hepten-4-ol having the structure:

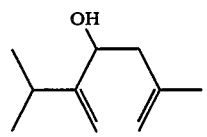

EXAMPLE IV

PREPARATION OF 2,6-DIMETHYL-5-METHYLENE-1-HEPTEN-4-YL ACETOACETATE

Reaction:

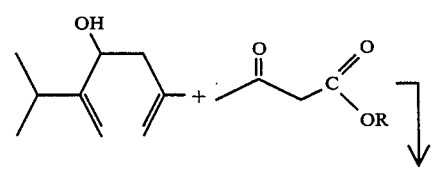

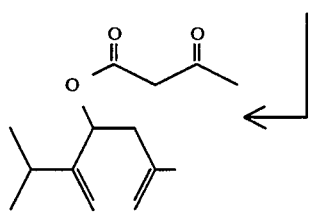

Methyl acetoacetate (700 grams) is added over a period of one hour to a mixture of xylene (1,300 ml), aluminum isopropylate (50 grams), and 2,6-dimethyl-1-hepten-4-ol (683 grams, produced according to Example III supra) at 100°-131° C. while distilling off the methanol through a 12" column packed with ¼" porcelain saddles at a vapor temperature below 70° C. The pot temperature is then increased to 150° C., and distillation of the methanol is continued until the vapor temperature reaches 95° C. (this takes approximately 4 hours). The reaction mass is cooled and poured into a mixture of crushed ice and 100 grams of 20% sulfuric acid solution.

The organic layer is then washed successively with water, saturated sodium bicarbonate solution and 10% sodium chloride solution. The solvent is removed on a rotary evaporator at reduced pressure, and the product is distilled using a 24" Goodloe packed column to give 690 grams of material which GLC analysis shows to contain 57% 2,6-dimethyl-5-methylene-1-hepten-4-yl acetoacetate having the structure:

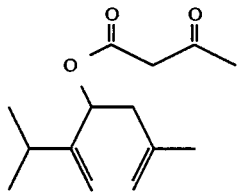

EXAMPLE V(A)

PREPARATION OF ISOSOLANONE (5-ISOPROPYL-8-METHYL-5,8-NONADIEN-2-ONE

Reaction:

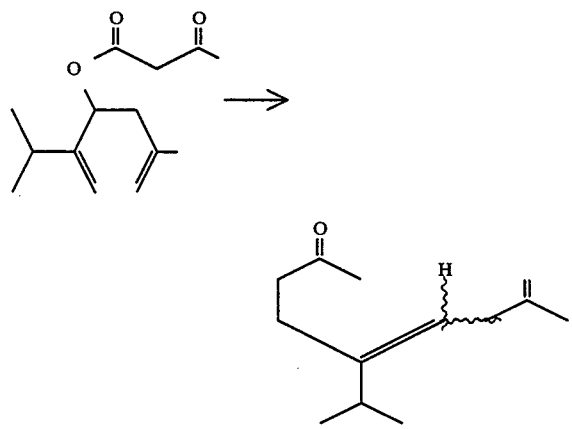

Into a 3 liter flask equipped with stirrer, thermometer, reflux condenser and heating mantle is placed 500 grams of N-methyl-2-pyrrolidinone and 10 grams of sodium carbonate. The resulting mixture is heated to 160° C., and over a period of one hour while maintaining the temperature at 160° C. with stirring, 1,310 grams of the compound having the structure:

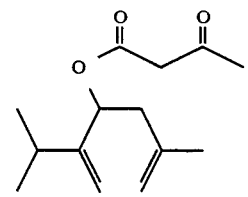

prepared according to Example IV (57.7% purity) is added to the reaction mass. The reaction mass is then refluxed at a temperature of 155°-170° C. for a period of 7 hours. At the end of this time, the reaction mass is cooled to room temperature.

An equal volume of water is added to the reaction mass. The reaction mass is then adjusted to a pH of 2 by addition of 10% sulfuric acid.

The reaction mass is filtered and washed two times with equal volumes of water. The toluene is stripped off and the reaction mass is rushed over using a 1' short path column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 62/66 | 91/100 | 4.0/3.2 | 109 |
| 2 | 84 | 122 | 3.0 | 213 |
| 3 | 103 | 145 | 3.6 | 134 |
| 4 | 135 | 224 | 5.5 | 196 |
| 5 | 148 | 235 | 3.6 | 43 |

Fractions 2–4 weighing 541 grams are bulked and then distilled on a 2' Goodloe column yielding the following fractions:

| Fraction Number | Vapor Temp. (°C.) | Liquid Temp. (°C.) | Pressure mm/Hg. | Reflux Ratio |
| --- | --- | --- | --- | --- |
| 1 | 40/52 | 87/89 | 3.0/2.6 | 4:1 |
| 2 | 58 | 93 | 3.6 | 4:1 |
| 3 | 58 | 98 | 3.4 | 4:1 |
| 4 | 58 | 106 | 3.3 | 4:1 |
| 5 | 70 | 110 | 3.1 | 4:1 |
| 6 | 87 | 112 | 3.0 | 4:1 |
| 7 | 88 | 112 | 3.0 | 4:1 |
| 8 | 90 | 115 | 2.8 | 4:1 |
| 9 | 90 | 119 | 2.8 | 4:1 |
| 10 | 91 | 138 | 2.8 | 3:1 |
| 11 | 98 | 142 | 2.8 | 4:1 |
| 12 | 99 | 154 | 2.8 | 9:1 |
| 13 | 105 | 155 | 2.8 | 9:1 |

NMR, IR, mass spectral and GLC analysis yield the information that the resulting reaction product is a mixture of cis and trans isomers defined according to the structure:

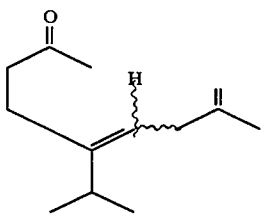

FIG. 5 is the GLC profile for bulked fractions 7–11 of the foregoing distillation (conditions: Carbowax column programmed at 100°–220° C.).

EXAMPLE V(B)

PREPARATION OF 5-ISOPROPYL-8-METHYL-5,8-NONADIEN-2-ONE

Reaction:

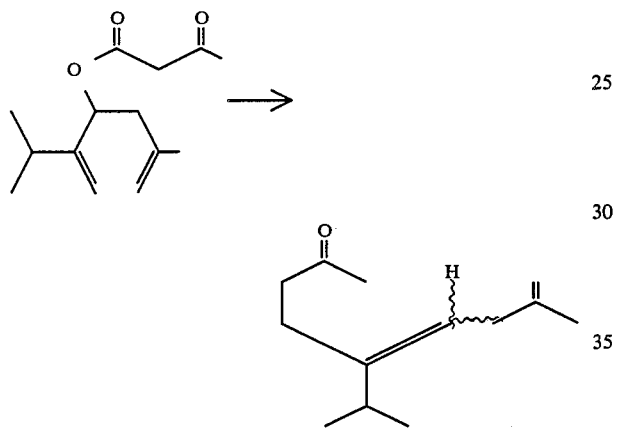

A mixture of 500 grams of 2,6-dimethyl-5-methylene-1-hepten-4-yl acetoacetate prepared according to Example IV and 10 grams of aluminum triisopropylate is heated to 150° C. at atmospheric pressure at which point carbon dioxide gas begins evolving. The mixture is heated to 195°–200° C. over a period of approximately three hours and is then held for approximately 30 minutes at 195°–200° C. Carbon dioxide evolution becomes very slow at this point. The reaction mass is then cooled, and the cooled reaction mass is poured into ice cold dilute aqueous acetic acid. The resulting organic layer is washed with water. The material is then distilled through a 24" Goodloe packed column to yield 214 grams of a material, b.p. 65°–94° C./3.2 mm/Hg. GLC analysis indicates that the product boiling over this range contains 84% 5-isopropyl-8-methyl-5,8-nonadien-2-one as a mixture of cis and trans isomers defined according to the structure:

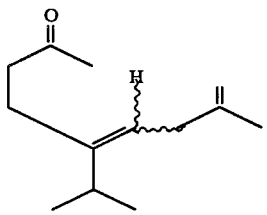

EXAMPLE VI(A)

PREPARATION OF ISOSOLANONE AND SOLANONE

Reaction:

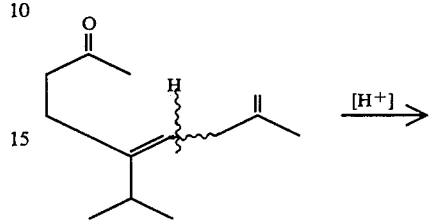

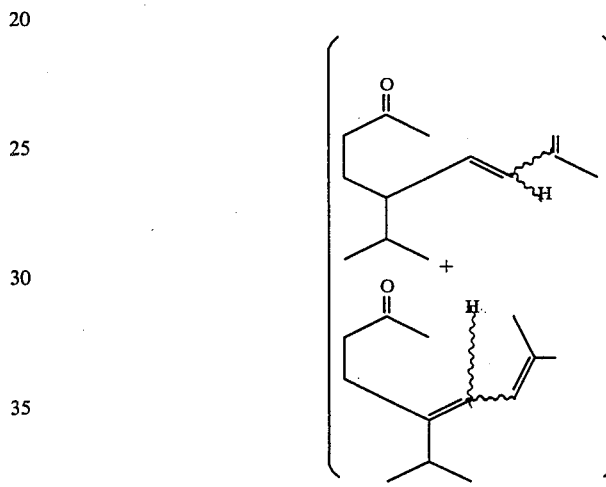

Into a 100 ml reaction flask equipped with stirrer, thermometer and reflux condenser is placed 20 ml toluene, 0.5 grams of para-toluenesulfonic acid and 20 grams of 5-isopropyl-8-methyl-5,8-nonadien-2-one having the structure:

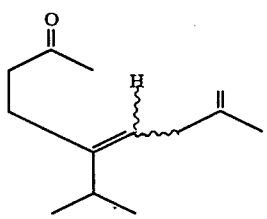

prepared according to Example V(B). The resulting mixture is stirred for a period of one hour at room temperature and then heated to 80°–82° C. and maintained at that temperature with stirring for a period of 8 hours. At this point the resulting product contains four compounds; cis and trans isosolanone defined according to the structures:

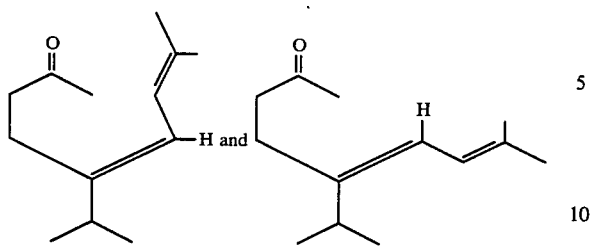

as well as cis and trans solanone having the structures:

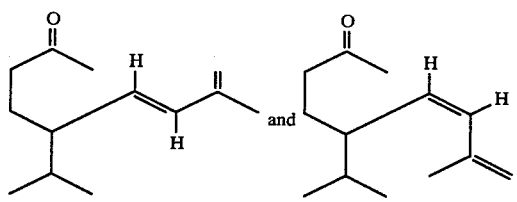

FIG. 6 is the GLC profile for the reaction product.
FIG. 7 is the NMR spectrum for peak 61 of the GLC profile of FIG. 6 for the cis or trans isomer of the compound having the structure:

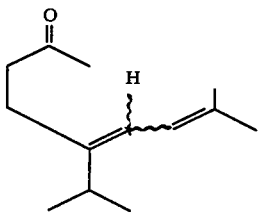

FIG. 8 is the NMR spectrum for the peak indicated by reference numeral "62" of FIG. 6 for the cis or trans isomer of the compound having the structure:

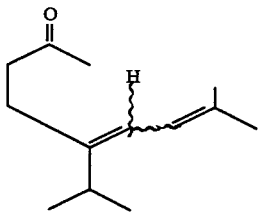

EXAMPLE VI(B)

PREPARATION OF 5-ISOPROPYL-8-METHYL-5,7-NONADIEN-2-ONE

Reaction:

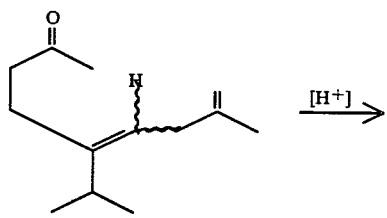

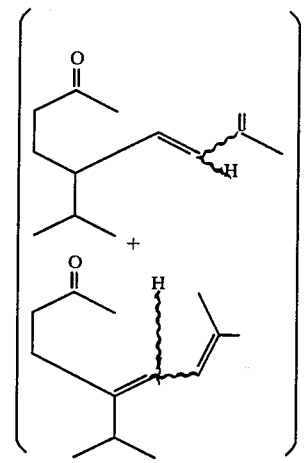

A mixture of 250 ml of toluene, 1 gram of para-toluenesulfonic acid and 214 grams of 5-isopropyl-8-methyl-5,8-nonadien-2-one produced according to Example V is stirred for approximately 8 hours at reflux (120°–121° C.).

The resulting reaction mass is then cooled to room temperature and washed with saturated sodium carbonate solution followed by 10% sodium chloride solution.

The resulting reaction product is distilled through a 24" Goodloe packed column yielding 141 grams of 5-isopropyl-8-methyl-5,7-nonadien-2-one as a mixture of cis and trans isomers.

EXAMPLE VII(A)

PREPARATION OF 8-METHYL-5-ISOPROPYL-5,8-NONADIEN-2-ONE (ONE STEP REACTION FROM 2,6-DIMETHYL-5-METHYLENE-1-HEPTEN-4-OL)

Reaction:

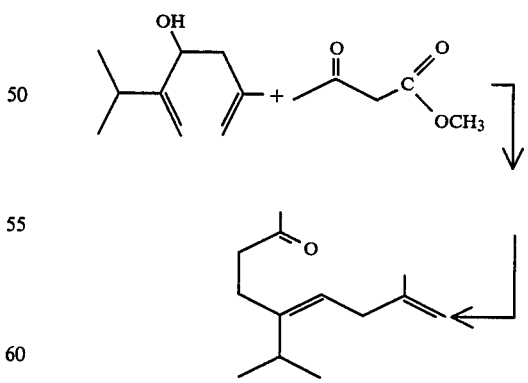

Into a 250 ml reaction flask equipped with stirrer, thermometer, reflux condenser and heating mantle is placed 52.0 grams (0.33 moles) of 2,6-dimethyl-5-methylene-1-hepten-4-ol (bulked fractions 5–7 of the distillation product of the reaction product prepared according to Example II), having the structure:

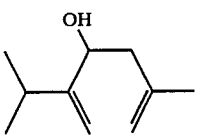

50 ml toluene and 2.0 grams of aluminum triisopropylate.

The resulting mixture is heated with stirring to 40° C. under a nitrogen blanket, and over a period of 20 minutes. 45.0 grams (0.33 moles) of methyl acetoacetate is added to the reaction mass. At the end of the addition the reaction mass is heated to reflux at 111°–120° C., and refluxing is continued for a period of two hours. At the end of the two hour period a Bidwell trap is fitted to the reaction flask and 100 ml of xylene is added to the reaction mass. The reaction mass is then heated to reflux and sufficient solvent is distilled off to increase the reaction temperature to 127°–130° C. for a period of five hours. At the end of this period the reaction mass is cooled to room temperature.

FIG. 9 is the GLC profile for the reaction product of this example containing the compounds having the structures:

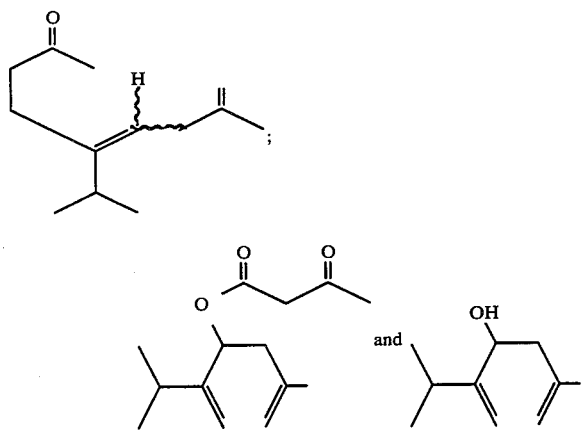

The peak on the GLC profile indicated by reference numeral "91" is a peak analyzed as a mixture of compounds, one having the structure:

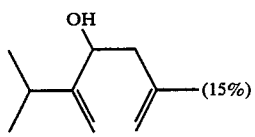

and the other having the structure:

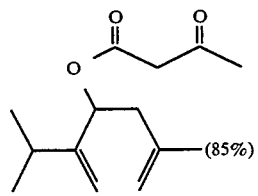

FIG. 10 is the NMR spectrum for peak 91 of FIG. 9 analyzed as a mixture of the compounds having the structures:

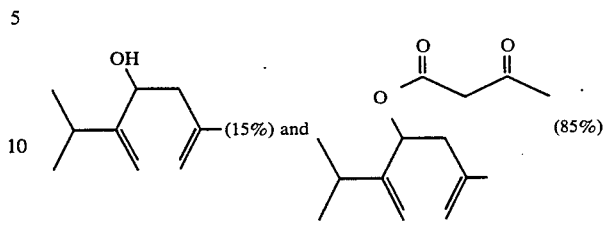

(Solvent: CFCl₃; Field strength: 100 MHz).

EXAMPLE VII(B)

PREPARATION OF 8-METHYL-5-ISOPROPYL-5,8-NONADIEN-2-ONE

Reaction:

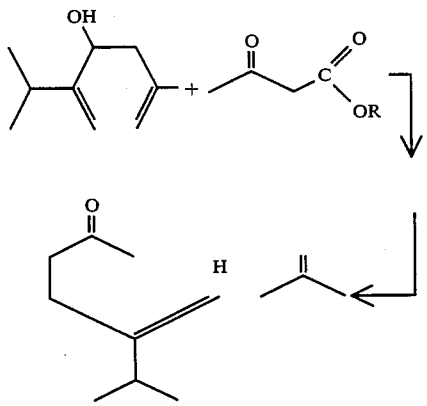

(wherein R represents ethyl).

Ethyl acetoacetate (176 grams) is added over a period of 20 minutes to a mixture of toluene (250 ml), aluminum isopropylate (10 grams), and 2,6-dimethyl-5-methylene-1-hepten-4-ol (prepared according to Example II; 205 grams) while maintaining the reaction mass at 115°–120° C.

While maintaining the reaction mass at a temperature of 115°–120° C. the resulting mixture is stirred for approximately 4 hours while distilling off the ethanol produced. 100 ml of xylene is then added, and reflux is continued for approximately 2 hours. An additional 179 grams of ethyl acetoacetate is added, and the mixture is heated at reflux (130°–137° C.) for a period of 6 hours. Heating is continued while removing low boiling material until the pot temperature reaches 200° C. (which takes approximately 2 hours) and then for an additional 1 hour at 200° C.

The reaction mass is then washed and distilled twice using a 36"×10 mm spinning band column to yield 113 grams of 5-isopropyl-8-methyl-5,8-nonadien-2-one (mixture of cis and trans isomers) defined according to the structure:

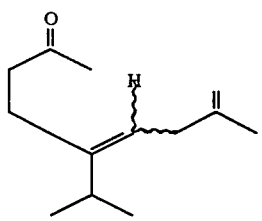

b.p. 82°-84° C. at 2.5 mm/Hg, 90% pure by GLC analysis.

The distillation fractions from the first distillation are as follows:

| Fraction Number | Vapor Temp. (°C.) | Liquid Temp. (°C.) | Pressure mm/Hg | Reflux Ratio |
|---|---|---|---|---|
| 1 | 20/18 | 80/100 | 2.0/7.0 | 20:1 |
| 2 | 64 | 112 | 4.6 | 20:1 |
| 3 | 80 | 115 | 3.2 | 20:1 |
| 4 | 90 | 113 | 3.3 | 20:1 |
| 5 | 92 | 121 | 3.2 | 20:1 |
| 6 | 92 | 123 | 3.2 | 20:1 |
| 7 | 92 | 134 | 3.2 | 20:1 |
| 8 | 90 | 168 | 3.2 | 20:1 |
| 9 | 81 | 220 | 3.2 | 20:1 |

Fractions 4–8 weighing 127 grams are bulked and redistilled.

The distillation fractions from the second distillation are as follows:

| Fraction Number | Vapor Temp. (°C.) | Liquid Temp. (°C.) | Pressure mm/Hg | Reflux Ratio | Weight of Fraction (grams) |
|---|---|---|---|---|---|
| 1 | 58 | 90/95 | 2.6/2.8 | 20:1 | 11.0 |
| 2 | 82 | 100 | 2.7 | 20:1 | 7.0 |
| 3 | 83 | 102 | 2.7 | 20:1 | 7.0 |
| 4 | 84 | 102 | 2.6 | 20:1 | 11.0 |
| 5 | 84 | 103 | 2.6 | 20:1 | 10.0 |
| 6 | 84 | 103 | 2.6 | 20:1 | 8.0 |
| 7 | 84 | 103 | 2.6 | 20:1 | 10.0 |
| 8 | 84 | 103 | 2.4 | 20:1 | 25.0 |
| 9 | 84 | 103 | 2.4 | 20:1 | 12.0 |
| 10 | 84 | 109 | 2.4 | 20:1 | 14.0 |
| 11 | 60 | 140 | 2.4 | 20:1 | 9.0 |

FIG. 11 is the GLC profile for bulked fractions 4–11 of the foregoing distillation (conditions: Carbowax column programmed at 100°-220° C.).

FIG. 12 is the NMR spectrum for fraction 7 of the foregoing distillation containing a mixture of cis and trans isomers of the compounds defined according to the structure:

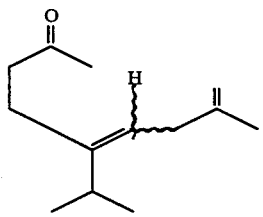

(Solvent: CFCl₃; Field strength: 100 MHz).

FIG. 13 is the infra-red spectrum for fraction 7 of the foregoing distillation containing a mixture of cis and trans isomers of compounds having the structure:

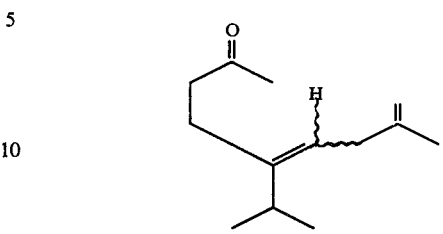

EXAMPLE VIII

PREPARATION OF 5-ISOPROPYL-8-METHYL-5,8-NONADIEN-2-ONE

Reactions:
Reaction IIIA'

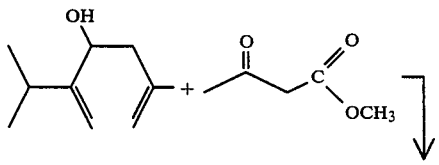

Reaction IIIB

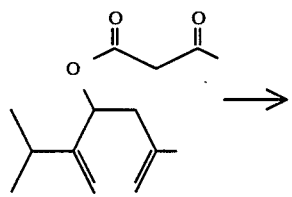

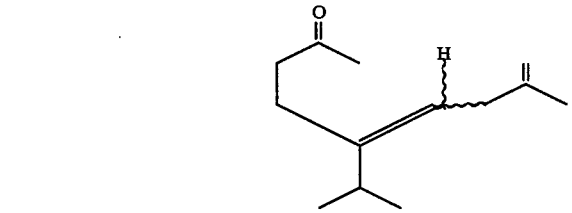

2,6-dimethyl-5-methylene-1-hepten-4-ol prepared according to Example II (875 grams; 93.6% by GLC analysis) is added over a one hour period to a mixture of toluene (1,300 ml), methyl acetoacetate (700 grams) and aluminum triisopropylate (50 grams) while maintaining the reaction mass at 110°-116° C.

The methanol which is generated is distilled off as formed using a 12" column packed with ¼" porcelain saddles, with the vapor temperature held below 70° C.

The reaction is heated for 7 hours at 120°-128° C. while continuing to collect the distillate at a vapor temperature below 70° C. An additional 80 grams of methyl acetoacetate is then added, and the reaction mass is heated to 156°-170° C. for 1 hour. The reaction mass is then cooled to room temperature and poured into aqueous sulfuric acid. The resulting organic layer is washed with water and then with a 10% sodium chloride solution. Residual solvent is removed on a rotary evaporator to yield 1,310 grams of crude 2,6-dimethyl-5-methylene-1-hepten-4-yl acetoacetate having the structure:

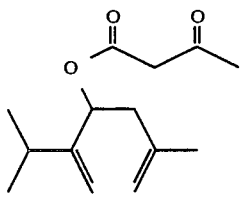

This crude ketoester is added over a period of 20 minutes to a mixture of 10 grams of sodium carbonate and 500 grams of N-methyl-2-pyrrolidinone while maintaining the reaction temperature at 150°-160° C.

Immediate evolution of carbon dioxide is observed. The reaction mass is stirred for approximately 7 hours at 150°-170° C. at which time the rate of carbon dioxide evolution becomes very slow. The reaction mass is cooled and diluted with water. The pH is adjusted to 2 by addition of 10% aqueous sulfuric acid solution. The reaction mass is filtered to remove solid material and the organic layer of the filtrate is washed twice with water. Toluene is added to improve phase separation during this work-up. The solvent is recovered, and the crude product is distilled twice to yield 243 grams of approximately 95% pure 5-isopropyl-8-methyl-5,8-nonadien-2-one as a mixture of cis and trans isomers defined according to the structures:

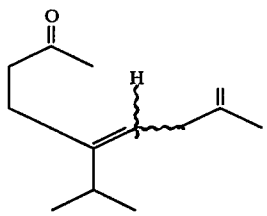

EXAMPLE IX

PREPARATION OF 5-ISOPROPYL-8-METHYL-5,7-NONADIEN-2-ONE ("ISOSOLANONE")

Reaction:

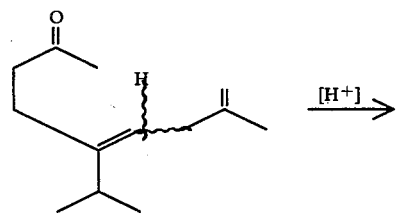

[H$^+$] →

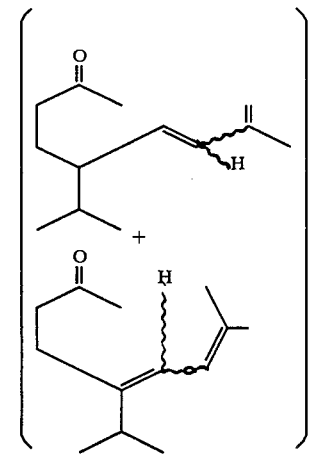

A mixture of 217 grams of the cis and trans isomers of 5-isopropyl-8-methyl-5,8-nonadien-2-one prepared according to Example VIII (98% pure by GLC), 250 ml of toluene and 1 gram of para-toluenesulfonic acid is stirred for approximately 1 hour at 80°-85° C. and for approximately 7 hours at reflux (120°-124° C.).

The reaction mass is then cooled, and the cooled mixture is washed successively with water and saturated sodium chloride solution. The resulting material is then distilled twice to give 150 grams of 5-isopropyl-8-methyl-5,7-nonadien-2-one boiling range 95°-109° C. at 33 mm/Hg pressure which is 88.9% pure by GLC analysis. NMR analysis of the two major peaks indicates that they are cis and trans isomers.

The first distillation as indicated above yields the following fractions:

| Fraction Number | Vapor Temp. (°C.) | Liquid Temp. (°C.) | Pressure mm/Hg | Weight of Fraction (grams) |
|---|---|---|---|---|
| 1 | 34/40 | 48/56 | 75.0 | 51.0 |
| 2 | 40 | 58 | 70.0 | 39.0 |
| 3 | 35 | 65 | 70.0 | 41.0 |
| 4 | 32 | 70 | 5.0 | 4.0 |
| 5 | 84 | 100 | 2.6 | 6.0 |
| 6 | 92 | 104 | 2.6 | 22.0 |
| 7 | 100 | 112 | 2.4 | 86.0 |
| 8 | 100 | 147 | 2.4 | 69.0 |
| 9 | 106 | 180 | 2.4 | 4.0 |

Fractions 6-9 are bulked (weight 180 grams) and then re-distilled on a 1' Goodloe column to yield the second distillation product having the following fractions:

| Fraction Number | Vapor Temp. (°C.) | Liquid Temp. (°C.) | Pressure mm/Hg. | Weight of Fraction (grams) |
|---|---|---|---|---|
| 1 | 63/72 | 104/108 | 2.8/2.8 | 4.0 |
| 2 | 79 | 109 | 2.8 | 5.0 |
| 3 | 35 | 109 | 3.0 | 12.0 |
| 4 | 97 | 109 | 3.0 | 7.0 |
| 5 | 97 | 109 | 3.0 | 11.0 |
| 6 | 98 | 109 | 3.0 | 9.0 |
| 7 | 101 | 112 | 3.2 | 11.0 |
| 8 | 101 | 112 | 3.0 | 14.0 |
| 9 | 101 | 114 | 3.0 | 21.0 |
| 10 | 103 | 122 | 2.8 | 20.0 |
| 11 | 108 | 125 | 2.8 | 25.0 |
| 12 | 109 | 126 | 2.8 | 20.0 |

| Fraction Number | Vapor Temp. (°C.) | Liquid Temp. (°C.) | Pressure mm/Hg. | Weight of Fraction (grams) |
|---|---|---|---|---|
| 13 | 109 | 210 | 2.8 | 17.0 |

FIG. 14 is the GLC profile for bulked fractions 9-12 of the foregoing distillation (conditions: SE-30 column programmed at 100°-220° C. at 8° C. per minute). The peak indicated by reference numeral "141" is the peak for either the cis or trans isomer of isosolanone having the structure:

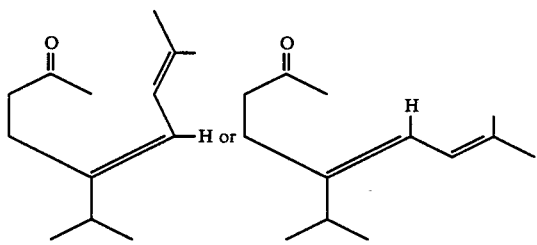

The peak indicated by reference numeral "142" is for either the cis or trans isomer of isosolanone having the structure:

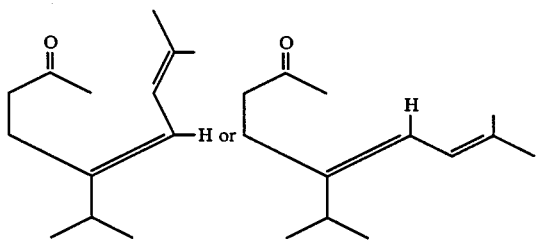

FIG. 15 is the NMR spectrum for the peak indicated by reference numeral "141" of FIG. 14 for the cis or trans isomer of the isosolanone having the structure:

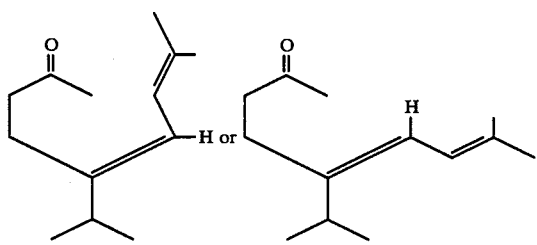

(Solvent: CFCl$_3$; Field strength: 100 MHz).

FIG. 16 is the NMR spectrum for the peak indicated by reference numeral "142" of FIG. 14 for the cis or trans isomer of isosolanone having the structure:

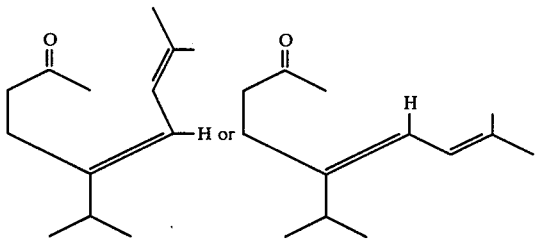

(Solvent: CFCl$_3$; Field strength: 100 MHz).

EXAMPLE X

The following rose formulation is prepared:

| Ingredients | Parts by Weight |
|---|---|
| Rhodinol | 250 |
| Phenylethyl alcohol | 195 |
| Alpha methyl ionone | 80 |
| Linalyl acetate | 60 |
| Cis-3-hexenyl acetate | 5 |
| Jasmine absolute | 10 |
| Cinnamic alcohol | 20 |
| Rhodinyl acetate | 60 |
| Cyclohexyl ethyl alcohol | 20 |
| Geraniol | 130 |
| Geranyl acetate | 80 |
| Paraisopropyl cyclohexanol | 60 |
| The alcohol prepared according to Example II having the structure: [structure with OH] bulked distillation fractions 3-8 | 30 |
| Trans,trans-delta-damascone (10% in diethyl phthalate) | 10 |

A similar perfume is prepared without the trans,trans-delta-damascone.

The compound having the structure.

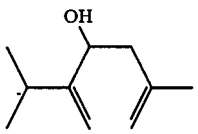

with or without the trans,trans-delta-damascone imparts minty, herbal, anisic, cedarleaf and pennyroyal-like nuances with coriander-like undertones to this floral composition. When the trans,trans-delta-damascone is added to the composition, it lends a sweet, floral, rose note to the fragrance composition in addition. The combination of the trans,trans-delta-damascone and the compound having the structure:

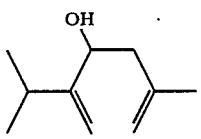

gives rise to a very interesting synergistic effect on this rose formulation making it much more intense and natural, fresh, Bulgarian rose-like.

EXAMPLE XI

One hundred grams of soap chips are intimately admixed with the various perfumery substances set forth in Table I below. The resulting mixtures under 8 atmospheres pressure, are heated to 180° C. and maintained at that temperature and pressure under a nitrogen atmosphere for a period of 3 hours. The resulting mass is then cooled and stamped into soap bars. Each of the soap bars prior to use and on use manifests an interesting aroma as set forth in Table I below:

TABLE I

| Perfumery Substance | Organoleptic Properties |
|---|---|
| Compound having the structure: OH [structure] prepared according to Example II, bulked fractions 3–8. | A minty, herbal, anisic, cedarleaf and pennyroyal-like aroma with floral and coriander-like undertones. |
| Perfume composition of Example X containing the compound having the structure: OH [structure] prepared according to Example II, bulked fractions 3–8, but not containing trans,trans-delta-damascone. | An intense floral aroma with minty, herbal, anisic, cedarleaf, pennyroyal-like and coriander nuances and intense coriander undertones. |
| Perfume composition of Example X containing both the compound having the structure: OH [structure] prepared according to Example II, bulked fractions 3–8, and trans,trans-delta-damascone. | A rose, floral aroma with minty, herbal, anisic, cedarleaf and pennyroyal-like topnotes and coriander undertones. |

EXAMPLE XII

PREPARATION OF A COSMETIC POWDER COMPOSITION

A cosmetic powder is prepared by mixing in a ball mill, 100 grams of talcum powder with 0.25 grams of one of the perfumery substances set forth in Table I of Example XI, supra. Each of the cosmetic powder samples has an excellent aroma as set forth in Table I of Example XI, supra.

EXAMPLE XIII

PERFUMED POLYMER

A melt of one hundred grams of polyethylene pellets is intimately admixed under 100 atmospheres pressure with one of the perfumery substances set forth in Table I of Example XI, supra. The resulting melt is stirred with the perfumery substance under 100 atmospheres pressure, the percentage of perfumery substance in the melt being 12% by weight. The agitation is carried out in a stirred, high pressure, thick walled, pressure vessel containing baffles. At the end of the mixing period, the resulting plastic perfume concentrate is extruded in droplets through orifices located in the apparatus whereby perfume-containing pellets are formed. The perfume-containing pellets are then molded into cores in accordance with the procedure of application for U.S. Pat. Ser. No. 362,263 filed on Mar. 26, 1982.

The resulting perfume-containing pellets exhibit perfumery properties as set forth in Table I of Example XI, supra. Application for U.S. Pat. Ser. No. 362,263 filed on Mar. 26, 1982 is hereby incorporated by reference herein.

EXAMPLE XIV

PERFUMED LIQUID DETERGENT

Concentrated liquid detergents (which detergents are produced from the lysine salt of n-dodecyl benzene sulfonic acid as more specifically described in U.S. Pat. No. 3,948,818 issued on Apr. 6, 1976, the specification for which is incorporated by reference herein) are prepared containing the perfumery substances as set forth in Table I of Example XI, supra. They are prepared by adding and homogeneously mixing the appropriate quantity of the perfumery substance of Table I of Example XI in the liquid detergent. The detergents all possess aromas as set forth in Table I of Example XI, the intensity increasing with greater concentrations of perfumery substance as set forth in Table I of Example XI, supra.

EXAMPLE XV

PREPARATION OF COLOGNES AND HANDKERCHIEF PERFUMES

Perfumery substances set forth in Table I of Example XI are individually incorporated into colognes at concentrations of 1.0%, 1.5%, 2.0%, 2.5%, 3.0%, 4.0% and 5.0% in 75%, 80%, 85% and 90% aqueous ethanol; and into handkerchief perfumes at concentrations of 10%, 15%, 20%, 25% and 30% (in 85%, 90% and 95% aqueous ethanol). Distinct and definitive aromas as set forth in Table I of Example XI are imparted to the cologne and to the handkerchief perfume samples.

EXAMPLE XVI

To the contents of a one pound can of HUNT'S ® red beets at levels of 0.5 ppm, 1 ppm and 2 ppm, the compound of Example II having the structure:

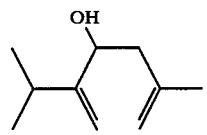

(distillation fraction 6) is added. The compound having the structure:

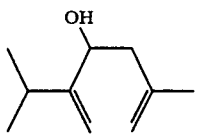

imparts to the canned red beets a much more natural-like, freshly harvested beet flavor making them much more organoleptically pleasing.

EXAMPLE XVII

GARLIC/ONION FLAVOR

The following ingredients are selected:

| Ingredients | Parts by Weight |
|---|---|
| Methyl-propyl disulfide | 2.0 |
| Methyl-propenyl disulfide | 0.5 |
| Dipropyl-disulfide | 86.0 |
| Compound having the structure:<br>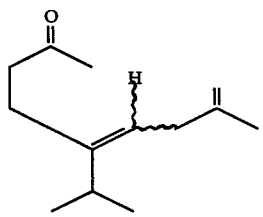<br>prepared according to Example VII(B), bulked fractions 7-10 | 7.0 |
| Propyl-propenyl disulfide | 4.0 |
| Diallyl-disulfide | 0.5 |

The ingredients are thoroughly and homogeneously mixed at 25° C. The mixture has an excellent onion/garlic flavor definitely enhanced over that obtained when the compound having the structure:

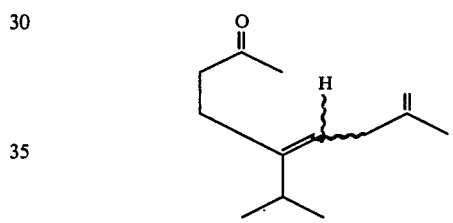

is omitted. The resulting flavor is incorporated into natural onion oil, and the onion oil is added to a baked French bread under 2 atmospheres pressure. The baked French bread has an interesting and novel onion/garlic nuance which is far improved over ordinary garlic oil or onion oil alone. It is noteworthy that no garlic oil is used herein.

EXAMPLES XVIII

ONION/GARLIC FLAVOR COMPOSITION

The following mixture is prepared:

| Ingredients | Parts by Weight |
|---|---|
| Dimethyl-disulfide | 4 |
| Methyl-propyl disulfide | 25 |
| Methyl-propenyl disulfide | 2 |
| Dipropyl-disulfide | 30 |
| Compound having the structure:<br><br>prepared according to Example V(A), supra (distillation fraction 9) | 15 |
| Diallyl-disulfide | 16 |
| Propyl-propenyl disulfide | 8 |

The ingredients are thoroughly and homogeneously mixed at 25° C. The mixture has an excellent onion/garlic flavor definitely enhanced over that obtained when the compound having the structure:

is omitted.

EXAMPLE XIX

The composition of Example XVIII is dissolved in propylene glycol in an amount sufficient to give a propylene glycol solution containing 0.1% by weight of said mixture, and 0.9 cc of this solution is added to 7.3 grams of a soup base consisting of:

| Ingredients | Parts by Weight |
|---|---|
| Fine ground sodium chloride | 35.62 |
| Hydrolyzed vegetable protein (4 BE:Nestle's) | 27.40 |
| Mono sodium glutamate | 17.81 |
| Sucrose | 10.96 |
| Beef fat | 5.48 |
| Sethness caramel color (powder B & C) | 2.73 |

The resulting mixture is added to 12 ounces of boiling water to create a soup having an excellent onion/garlic flavor.

A composition the same as that of Example XVIII is prepared except it contains in addition, 5% by weight of natural garlic oil. When added to the above soup base, and the mixture added to boiling water, a soup base having an excellent natural garlic/onion flavor is prepared having a novel, aesthetically pleasing taste and aroma.

EXAMPLE XX 0.5 grams of the mixture of Example XVII is emulsified in a solution containing the following materials:
- 100 grams gum arabic
- 100 grams water
- 0.5 grams of a 20% solution in ethanol of butylated hydroxy anisole The resulting emulsion is spray-dried in a Bowen Lab. Model spray-drier, inlet temperature 500° F., outlet temperature 200° F. Twelve grams of this spray-dried material is mixed with 29.2 grams of the soup base as set forth in Example XIX. The resulting mixture is then added to 12 ounces of boiling water and an excellent onion/garlic flavored soup is obtained.

EXAMPLE XXI 330 grams of gelatin is dissolved at 40° C. in 8,250 grams of deionized water to form a "gelatin solution".

330 grams of a spray-dried gum arabic is dissolved at room temperature in 8,250 grams of deionized water to form a "gum arabic solution".

The gum arabic solution is placed in a 30 liter vessel and 2.5 liters of the gelatin solution is added. The temperature of the mixture is adjusted to 37°–40° C. Through a tube beneath the surface of the gum arabic solution, 4,000 grams of a 0.1% (by weight) solution of the mixture of Example XVIII and propylene glycol is added over a period of approximately 30 minutes.

The mixture is agitated at 37°–40° C. until an average droplet size of 25 microns is obtained. The remaining gelatin solution (6 liters) is then added. The pH of the solution is then adjusted to 4.5 to 4.6 with a 10% sodium hydroxide solution.

After the 25 micron droplet size is achieved, the temperature is allowed to drop to 25° C. over a period of approximately 25 hours while maintaining the pH at 4.5 to 4.6.

The capsule slurry is then stirred and cooled to 5° C. and is maintained at 5° C. with stirring for at least 2.5 hours. The slurry is then spray-dried.

The capsules thus formed are filtered and mixed with the soup base of Example XIX in the weight ratio of 1:6. Twenty grams of the resulting capsule-soup base mixture is then added to 30 ounces of boiling water thereby creating a soup having an excellent onion/garlic flavor.

EXAMPLE XXII

The following ingredients are selected and mixed as described in Example XVIII and yield a composition having an excellent onion/garlic flavor.

| Ingredients | Parts by Weight |
| --- | --- |
| A. Methyl propenyl disulfide | 5 |
| Methyl propenyl trisulfide | 5 |
| 3,4-dimethyl thiophene | 1 |
| Dimethyl disulfide | 12 |
| Dipropyl disulfide | 32 |
| Compound having the structure: [structure] prepared according to Example VII(B), bulked fractions 7–10 | 44 |
| B. Propyl propenyl disulfide | 15 |
| Methyl propenyl disulfide | 5 |
| Propyl propenyl trisulfide | 5 |
| Dipropyl disulfide | 10 |
| Corn oil | 40 |
| Compound having the structure: [structure] prepared according to Example V(A), distillation fraction 9 | 25 |
| C. Methyl propenyl trisulfide | 9 |
| Propyl propenyl trisulfide | 9 |
| Propyl propenyl disulfide | 15 |
| Dimethyl disulfide | 1 |
| Diallyl disulfide | 1 |
| Gum arabic | 40 |
| Compound having the structure: [structure] prepared according to Example VII(B), bulked fractions 7–10 | 25 |

EXAMPLE XXIII

TOBACCO FORMULATION

A tobacco mixture is prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. One-third of the cigarettes are then treated with 750 ppm of a 50:50 weight:weight mixture of trans,trans-delta-damascone produced according to Example X of U.S. Pat. No. 4,211,242, the disclosure of which is incorporated by reference herein and the reaction product of Example IX, bulked fractions 4–13 of the distillation product containing a mixture of cis and trans isomers of compounds having the structure:

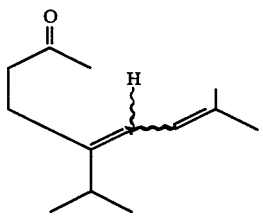

Another third of the cigarettes is then treated with 750 ppm of a mixture of cis and trans isomers having the structure:

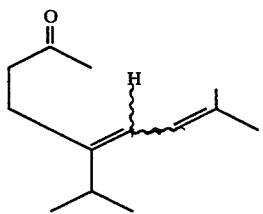

produced according to Example IX, bulked fractions 4–13. The last third of the cigarettes are termed "control cigarettes", the control cigarettes not containing either trans,trans-delta-damascone or the compounds defined according to the structure:

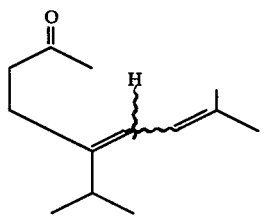

and the experimental cigarettes which contain either the mixture of trans,trans-delta-damascone and the compounds having the structure:

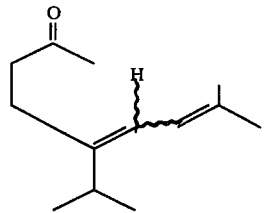

or the compounds having the structure:

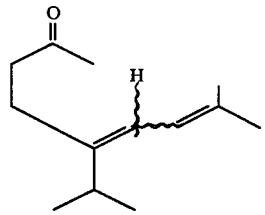

without the trans,trans-delta-damascone are evaluated by paired comparison and the results are as follows:

The experimental cigarettes both with and without the trans,trans-delta-damascone are found to have more body and tobacco smoke flavor and a fuller body sensation; much richer in body than the control cigarettes.

The tobacco-like notes are enhanced in the experimental cigarettes, and the flavor of tobacco, on smoking, is more aromatic with musty, slightly green, full-bodied burley tobacco notes. In addition, fruity notes and hay-tea-like aroma and taste nuances are added when the trans,trans-delta-damascone is used.

The tobacco smoke flavor of the experimental cigarettes prior to smoking has in the case of using the mixture of trans,trans-delta-damascone and the mixture of cis and trans isomers having the structure:

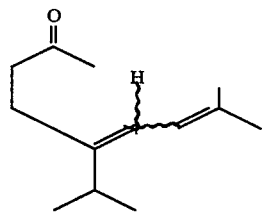

a floral, musty, hay-tea-like, sweet, slightly green, burley tobacco-like and fruity aroma and taste profile.

All cigarettes are evaluated for smoke flavor with a 20 mm cellulose acetate filter.

What is claimed is:

1. A process for augmenting or enhancing the aroma of a consumable material selected from the group consisting of perfume compositions, colognes and perfumed articles comprising to the step of adding to said consumable material, an aroma augmenting or enhancing quantity of the compound having the structure:

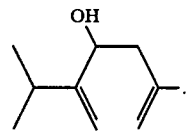

2. The process of claim 1 wherein the consumable material is a perfume composition, cologne or perfumed polymer.

3. The process of claim 1 wherein the consumable material is a perfumed article and the perfumed article is a solid or liquid anionic, cationic, nonionic or zwitterionic detergent.

4. The process of claim 1 wherein the consumable material is a perfumed article and the perfumed article is a fabric softener composition or fabric softener article.

5. The process of claim 1 wherein there is also added to the compound having the structure:

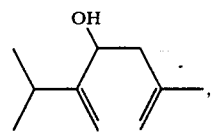

trans, trans-delta damascone.

6. The process of claim 5 wherein the consumable material is a perfume composition, cologne or perfumed polymer.

7. The process of claim 5 wherein the consumable material is a perfumed article and the perfumed article is a solid or liquid anionic, cationic, nonionic or zwitterionic detergent.

8. The process of claim 5 wherein the consumable material is a perfumed article and the perfumed article is a fabric softener composition or fabric softener article.

* * * * *